US008936792B2

(12) United States Patent
Pastan et al.

(10) Patent No.: US 8,936,792 B2

(45) Date of Patent: Jan. 20, 2015

(54) ***PSEUDOMONAS* EXOTOXIN A WITH REDUCED IMMUNOGENICITY**

(75) Inventors: Ira H. Pastan, Potomac, MD (US); Richard Beers, Rockville, MD (US); Masanori Onda, Rockville, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 382 days.

(21) Appl. No.: 13/395,422

(22) PCT Filed: Sep. 10, 2010

(86) PCT No.: PCT/US2010/048504

§ 371 (c)(1), (2), (4) Date: Jun. 25, 2012

(87) PCT Pub. No.: WO2011/032022

PCT Pub. Date: Mar. 17, 2011

(65) Prior Publication Data

US 2012/0263674 A1 Oct. 18, 2012

Related U.S. Application Data

(60) Provisional application No. 61/241,620, filed on Sep. 11, 2009.

(51) Int. Cl.

| | |
|---|---|
| ***A61K 39/108*** | (2006.01) |
| ***C07K 14/21*** | (2006.01) |
| *A61K 38/00* | (2006.01) |

(52) U.S. Cl.

CPC *C07K 14/21* (2013.01); *A61K 38/00* (2013.01)

USPC .................. 424/260.1; 424/235.1; 424/236.1; 424/185.1; 424/190.1; 424/192.1; 424/193.1; 424/195.11; 424/198.1; 530/350; 530/387.1; 530/387.3

(58) Field of Classification Search

None

See application file for complete search history.

(56) References Cited

U.S. PATENT DOCUMENTS

| | | | |
|---|---|---|---|
| 4,235,871 | A | 11/1980 | Papahadjopoulos et al. |
| 4,501,728 | A | 2/1985 | Geho et al. |
| 4,816,567 | A | 3/1989 | Cabilly et al. |
| 4,837,028 | A | 6/1989 | Allen |
| 4,892,827 | A | 1/1990 | Pastan et al. |
| 4,902,505 | A | 2/1990 | Pardridge et al. |
| 4,957,735 | A | 9/1990 | Huang |
| 5,004,697 | A | 4/1991 | Pardridge |
| 5,019,369 | A | 5/1991 | Presant et al. |
| 5,055,303 | A | 10/1991 | Riley, Jr. |
| 5,188,837 | A | 2/1993 | Domb |
| 5,242,824 | A | 9/1993 | Hellstrom et al. |
| 5,254,342 | A | 10/1993 | Shen et al. |
| 5,268,164 | A | 12/1993 | Kozarich et al. |
| 5,271,961 | A | 12/1993 | Mathiowitz et al. |
| 5,413,797 | A | 5/1995 | Khan et al. |
| 5,506,206 | A | 4/1996 | Kozarich et al. |
| 5,512,658 | A | 4/1996 | Pastan et al. |
| 5,514,670 | A | 5/1996 | Friedman et al. |
| 5,530,101 | A | 6/1996 | Queen et al. |
| 5,534,496 | A | 7/1996 | Lee et al. |
| 5,585,089 | A | 12/1996 | Queen et al. |
| 5,591,828 | A | 1/1997 | Bosslet et al. |
| 5,602,095 | A | 2/1997 | Pastan et al. |
| 5,608,039 | A | 3/1997 | Pastan et al. |
| 5,693,762 | A | 12/1997 | Queen et al. |
| 5,747,654 | A | 5/1998 | Pastan et al. |
| 5,821,238 | A | 10/1998 | Pastan et al. |
| 5,846,535 | A | 12/1998 | Pastan et al. |
| 5,854,044 | A | 12/1998 | Pastan et al. |
| 5,859,205 | A | 1/1999 | Adair et al. |
| 5,888,773 | A | 3/1999 | Jost et al. |
| 5,889,157 | A | 3/1999 | Pastan et al. |
| 5,981,726 | A | 11/1999 | Pastan et al. |
| 5,990,296 | A | 11/1999 | Pastan et al. |
| 6,083,502 | A | 7/2000 | Pastan et al. |
| 6,153,430 | A | 11/2000 | Pastan et al. |
| 6,180,377 | B1 | 1/2001 | Morgan et al. |
| 6,407,213 | B1 | 6/2002 | Carter et al. |
| 6,518,061 | B1 | 2/2003 | Puri et al. |
| 6,558,672 | B1 | 5/2003 | Pastan et al. |
| 6,809,184 | B1 | 10/2004 | Pastan et al. |
| 7,081,518 | B1 | 7/2006 | Pastan et al. |
| 7,355,012 | B2 | 4/2008 | Pastan et al. |
| 7,368,110 | B2 | 5/2008 | Pastan et al. |
| 7,470,775 | B2 | 12/2008 | Pastan et al. |
| 7,521,054 | B2 | 4/2009 | Pastan et al. |

(Continued)

FOREIGN PATENT DOCUMENTS

| | | |
|---|---|---|
| EP | 0173494 | 3/1986 |
| EP | 0404097 | 12/1990 |
| WO | WO 87/02671 | 5/1987 |

(Continued)

OTHER PUBLICATIONS

Altschul et al., "Basic local alignment search tool," *J. Mol. Biol.*, 215 (3), 403-410 (1990).

Altschul et al., "Gapped BLAST and PSI-BLAST: a new generation of protein database search programs," *Nucl. Acids Res.*, 25 (17), 3389-3402 (1997).

Arndt et al., "Helix-stabilized Fv (hsFv) antibody fragments: substituting the constant domains of a Fab fragment for a heterodimeric coiled-coil domain," *J. Mol. Biol.*, 312 (1), 221-228 (2001).

Beaucage et al., "Deoxynucleoside phosphoramidites—A new class of key intermediates for deoxypolynucleotide synthesis," *Tetra. Lett.*, 22 (20), 1859-1862 (1981).

Brinkman et al., "Cloning and expression of the recombinant FAb fragment of monoclonal antibody K1 that reacts with mesothelin present on mesotheliomas and ovarian cancers," *Int. J. Cancer*, 71 (4), 638-644 (1997).

(Continued)

*Primary Examiner* — Jennifer Graser

(74) *Attorney, Agent, or Firm* — Leydig, Voit & Mayer

(57) ABSTRACT

The present invention provides improved *Pseudomonas* Exotoxin A (PE) molecules with high cytotoxicity and reduced immunogenicity, compositions containing the improved (PE), and methods of use.

37 Claims, 6 Drawing Sheets

(56) References Cited

U.S. PATENT DOCUMENTS

| | | | |
|---|---|---|---|
| 7,541,034 | B1 | 6/2009 | Fitzgerald et al. |
| 2007/0189962 | A1 | 8/2007 | Pastan et al. |

FOREIGN PATENT DOCUMENTS

| | | |
|---|---|---|
| WO | WO 93/11161 | 6/1993 |
| WO | 96/04313 A1 | 2/1996 |
| WO | WO 97/25068 | 7/1997 |
| WO | WO 98/45322 | 10/1998 |
| WO | WO 99/51643 | 10/1999 |
| WO | WO 01/34645 | 5/2001 |
| WO | WO 03/027135 | 4/2003 |
| WO | WO 03/039600 | 5/2003 |
| WO | WO 2005/052006 | 6/2005 |
| WO | WO 2007/016150 | 2/2007 |
| WO | WO 2009/032954 | 3/2009 |

OTHER PUBLICATIONS

Brinkmann, "Recombinant immunotoxins: protein engineering for cancer therapy," *Mol. Med. Today*, 2 (10), 439-446 (1996).

Brown et al., "Chemical synthesis and cloning of a tyrosine tRNA gene," Methods *Enzymol.*, 68, 109-151 (1979).

Buchner et al., "A method for increasing the yield of properly folded recombinant fusion proteins: single-chain immunotoxins from renaturation of bacterial inclusion bodies," *Anal. Biochem.*, 205 (2), 263-270 (1992).

Chang et al., "Molecular cloning and expression of a cDNA encoding a protein detected by the K1 antibody from an ovarian carcinoma (OVCAR-3) cell line," *Int. J. Cancer*, 57 (1), 90-97 (1994).

Chang et al., "Molecular cloning of mesothelin, a differentiation antigen present on mesothelium, mesotheliomas, and ovarian cancers," *Proc. Nat'l Acad. Sci. USA*, 93 (1), 136-140 (1996).

Chowdhury et al., "Isolation of a high-affinity stable single-chain Fv specific for mesothelin from DNA-immunized mice by phage display and construction of a recombinant immunotoxin with anti-tumor activity," *Proc. Nat'l Acad. Sci. USA*, 95 (2), 669-674 (1998).

Chowdhury et al., "Isolation of anti-mesothelin antibodies from a phage display library," *Mol. Immunol.*, 34 (1), 9-20 (1997).

Davies et al., "Antibody VH Domains as Small Recognition Units," *Biotechnology*, 13, 475-479 (1995).

Ellison et al., "Linkage and sequence homology of two human immunoglobulin γ heavy chain constant region genes," *Proc. Nat'l Acad. Sci. USA*, 79, 1984-1988 (1982).

Ellison et al., "Nucleotide sequence of a human immunoglobulin Cγ4 gene," *DNA*, 1 (1), 11-18 (1981).

Ellison et al., "The nucleotide sequence of a human immunoglobulin Cγ1 gene," *Nucl. Acids Res.*, 10 (13), 4071-4079 (1982).

Feng et al., "A novel human monoclonal antibody that binds with high affinity to mesothelin-expressing cells and kills them by antibody-dependent cell-mediated cytotoxicity," *Mol. Cancer Ther.*, 8 (5), 1113-1118 (2009).

Frankel et al., "Targeted toxins," *Clin. Cancer Res.*, 6 (2), 326-334 (2000).

Fults et al., "Sustained-Release of Urease from a Poloxamer Gel Matrix," *J. Parent. Sci. Tech.*, 44 (2), 58-65 (1990).

Genbank Accession No. NM_001100374.1 (printed Aug. 26, 2012).

Genbank Accession No. NM_005823.4 (printed Mar. 4, 2010).

Genbank Accession No. NM_013404.3 (printed Mar. 4, 2010).

Genbank Accession No. NM_018857.1 (printed Sep. 2, 2012).

Genbank Accession No. NM_031658.1 (printed Apr. 22, 2012).

Genbank Accession No. NP_001093844.1 (printed Aug. 26, 2012).

Genbank Accession No. NP_005814.2 (printed Oct. 21, 2012).

Genbank Accession No. NP_037536.2 (printed Nov. 12, 2012).

Genbank Accession No. NP_061345.1 (printed Sep. 2, 2012).

Genbank Accession No. NP_113846.1 (printed Apr. 22, 2012).

Ghahroudi et al., "Selection and identification of single domain antibody fragments from camel heavy-chain antibodies," *FEBS Lett.*, 414, 521-526 (1997).

Hansen et al., "A Recombinant Immunotoxin Targeting CD22 with low Immunogenicity, Low Nonspecific Toxicity, and High Antitumor Activity in Mice," *J. Immunother.*, 33 (3) 297-304 (2010).

Harmsen et al., "Properties, production, and applications of camelid single-domain antibody fragments," *Appl. Microbiol. Biotechnol.* 77 (1), 13-22 (2007).

Hassan et al., "Antitumor activity of SS(dsFv)PE38 and SS1(dsFv)PE38, recombinant antimesothelin immunotoxins against human gynecologic cancers grown in organotypic culture in vitro," *Clin. Cancer Res.* , 8(11), 3520-3526 (2002).

Hassan et al., "SS1(dsFv)-PE38 anti-mesothelin immunotoxin in advanced malignancies: phase 1 and pharmacokinetic study of alternate-day infusion," *Proc. Am. Soc. Clin. Oncol.*, 21, 29a (2002).

Henikoff et al., "Amino acid substitution matrices from protein blocks," *Proc. Natl. Acad. Sci. USA*, 89 (22), 10915-10919 (1992).

Holliger et al., "Diabodies: small bivalent and bispecific antibody fragments," *Proc. Natl. Acad. Sci. USA*, 90, 6444-6448 (1993).

Holt et al., "Domain antibodies: proteins for therapy," *Trends Biotech.*, 21 (11), 484-490 (2003).

Honjo et al., "Cloning and complete nucleotide sequence of mouse immunoglobulin γl chain gene," *Cell*, 18 (2), 559-568 (1979).

Huse et al., "Generation of a Large Combinatorial Library of the Immunoglobulin Repertoire in Phage Lambda," *Science*, 246, 1275-1281 (1989).

Hwang et al., "Functional domains of *Pseudomonas* exotoxin identified by deletion analysis of the gene expressed in *E. coli," Cell*, 48 (1), 129-136 (1987).

Ijntema et al., "Hydroxyapatite microcarriers for biocontrolled release of protein drugs," *Int. J. Pharm.*, 112 (3), 215-224 (1994).

International Preliminary Report on Patentability, Application No. PCT/US2010/048504, dated Mar. 13, 2012.

International Search Report, Application No. PCT/US2010/048504, dated Mar. 17, 2011.

Johnston et al., "Sustained delivery of interleukin-2 from a poloxamer 407 gel matrix following intraperitoneal injection in mice," *Pharm. Res.*, 9 (3), 425-434 (1992).

Jones et al., "Replacing the complementarity-determining regions in a human antibody with those from a mouse," *Nature*, 321 (6069), 522-525 (1986).

Karlin et al., "Applications and statistics for multiple high-scoring segments in molecular sequences," *Proc. Natl. Acad. Sci. USA*, 90, 5873-5787 (1993).

Kondo et al., "Activity of immunotoxins constructed with modified *Pseudomonas* exotoxin a lacking the cell recognition domain," *J. Biol. Chem.*, 263 (19), 9470-9475 (1988).

Kreitman et al., "Efficacy of the anti-CD22 recombinant immunotoxin BL22 in chemotherapy-resistant hairy-cell leukemia," *New Engl. J. Med.*, 345 (4), 241-247 (2001).

Kreitman, "Immunotoxins for targeted cancer therapy," *AAPS Journal*, 8 (3), E532-E551 (2006).

Langer, "Polymer-controlled drug delivery systems," *Acc. Chem. Res.*, 26 (10), 537-542 (1993).

Lauwereys et al., "Potent enzyme inhibitors derived from dromedary heavy-chain antibodies," *EMBO J.*, 17 (13), 3512-3520 (1998).

Li et al., "The epitope specificity and tissue reactivity of four murine monoclonal anti-CD22 antibodies," *Cell. Immunol.*, 118 (1), 85-99 (1989).

Mansfield et al., "Recombinant RFB4 immunotoxins exhibit potent cytotoxic activity for CD22-bearing cells and tumors," *Blood*, 90 (5), 2020-2026 (1997).

Merrifield, "Solid Phase Peptide Synthesis. I. The Synthesis of a Tetrapeptide," *J. Am. Chem. Soc.*, 85, 2149-2154 (1963).

Mufson, "Tumor antigen targets and tumor immunotherapy," *Front Biosci.*, 11, 337-343 (2006).

Nagata et al., "Removal of B cell epitopes as a practical approach for reducing the immunogenicity of foreign protein-based therapeutics," *Adv. Drug Del. Rev.*, 61 (11), 977-985 (2009) (Author Manuscript).

Narang et al., "Improved phosphotriester method for the synthesis of gene fragments," *Methods. Enzymol.*, 68, 90-98 (1979).

Needham-Vandevanter et al., "Characterization of an adduct between CC-1065 and a defined oligodeoxynucleotide duplex," *Nucl. Acids Res.*, 12 (15), 6159-6168 (1984).

(56) References Cited

OTHER PUBLICATIONS

Needleman et al., "A General Method Applicable to the Search for Similiarities in the Amino Acid Sequence of Two Proteins," *J. Mol. Biol.*, 48, 443-453 (1970).
Onda et al., "An Immunotoxin with greatly reduced immunogenicity by identification and removal of B Cell epitopes," *Proc. Nat'l Acad. Sci., USA*, 105 (32), 11311-11316 (2008).
Onda et al., "Characterization of the B Cell Epitopes Associated with a Truncated Form of *Pseudomonas* Exotoxin (PE38) Used to Make Immunotoxins for the Treatment of Cancer Patients," *J. Immunol.*, 177, 8822-8834 (2006).
Onda et al., "Lowering the isoelectric point of the Fv portion of recombinant immunotoxins leads to decreased nonspecific animal toxicity without affecting antitumor activity," *Cancer Res.*, 61 (13), 5070-5077 (2001).
Pai et al., "Anti-tumor activities of immunotoxins made of monoclonal antibody B3 and various forms of *Pseudomonas* exotoxin," *Proc. Natl. Acad. Sci. USA*, 88 (8), 3358-3362 (1991).
Pastan, "Targeted therapy of cancer with recombinant immunotoxins," *Biochim. Biophys. Acta*, 1333 (2), C1-C6 (1997).
Pearson et al., "Improved tools for biological sequence comparison," *Proc. Natl. Acad. Sci. USA*, 85 (8), 2444-2448 (1988).
Plückthun, "Antibody engineering: advances from the use of *Escherichia coli* expression systems," *Bio/Technology*, 9 (6), 545-551 (1991).
Riechmann et al., "Reshaping human antibodies for therapy," *Nature*, 332 (6162), 323-327 (1988).
Reiter et al., "An antibody single-domain phage display library of a native heavy chain variable region: isolation of functional single-domain VH molecules with a unique interface," *J. Mol. Biol.*, 290 (3), 685-698 (1999).
Saerens et al., "Single-domain antibodies as building blocks for novel therapeutics," *Curr. Opin. Pharmacol.*, 8 (5), 600-608 (2008).
Salvatore et al., "Improved cytotoxic activity toward cell lines and fresh leukemia cells of a mutant anti-CD22 immunotoxin obtained by antibody phage display," *Clin. Cancer Res.*, 8 (4), 995-1002 (2002).
Saxena et al., "Formation of three-dimensional structure in proteins. I. Rapid nonenzymic reactivation of reduced lysozyme," *Biochemistry*, 9 (25), 5015-5022 (1970).
Siegall et al., "Functional analysis of domains II, Ib, and III of *Pseudomonas* exotoxin," *J. Biol. Chem.*, 264 (24), 14256-14261 (1989).
Smith et al., "Comparison of Biosequences," *Adv. Appl. Math.*, 2, 482-489 (1981).
Thomas et al., "Mesothelin-specific CD8(+) T cell responses provide evidence of in vivo cross-priming by antigen-presenting cells in vaccinated pancreatic cancer patients," *J. Exp. Med.*, 200 (3), 297-306 (2004).
Tucker et al., "Sequence of the cloned gene for the constant region of murine γ2b immunoglobulin heavy chain," *Science*, 206 (4424), 1303-1306 (1979).
Vaickus et al., "Immune markers in hematologic malignancies," *Crit. Rev. Oncol/Hematol.*, 11 (4), 267-297 (1991).
Vaughan et al., "Human antibodies with sub-nanomolar affinities isolated from a large non-immunized phage display library," *Nat. Biotechnol.*, 14 (3), 309-314 (1996).
Verhoeyen et al., Reshaping human antibodies: grafting an antilysozyme activity,' *Science*, 239 (4847), 1534-1536 (1988).
Ward et al., "Binding activities of a repertoire of single immunoglobulin variable domains secreted from *Escherichia coli,*" *Nature*, 341, 544-546 (1989).
Weldon et al., "A protease-resistant immunotoxin against CD22 with greatly increased activity against CLL and diminished animal toxicity," *Blood*, 113 (16), 3792-3800 (2009).
Weldon et al., "A protease-resistant immunotoxin against CD22 with greatly increased activity against CLL and diminished animal toxicity," *Blood*, 113 (16), 3792-3800 (2009) (First Edition Prepublication 2008).
Wesolowski et al., "Single domain antibodies: promising experimental and therapeutic tools in infection and immunity," *Med Microbiol. Immunol.*, 198 (3), 157-174 (2009).
Winter et al., "Man-made antibodies," *Nature*, 349 (6307), 293-299 (1991).
Written Opinion of the International Searching Authority, Application No. PCT/US2010/048504, dated Mar. 11, 2012.
Yamao et al., "UGA is read as tryptophan in Mycoplasma capricolum," *Proc. Nat'l Acad. Sci. USA*, 82 (8), 2306-2309 (1985).
Yamawaki-Kataoke et al., "Complete nucleotide sequence of immunoglobulin γ2b chain gene cloned from newborn mouse DNA," *Nature*, 283 (5749), 786-789 (1980).
Snell et al, "Role of Exotoxin and Protease as Possible Virulence Factors in Experimental Infections with *Pseudomonas aeruginosa,*" *Infection and Immunity*, 19(3): 839-845, (Mar. 1978).
Friedman et al., "BR96 sFv-PE49, a Potent Single-Chain Immunotoxin That Selectively Kills Carcinoma Cells," *Cancer Research*, 53: 334-339, (Jan. 15, 1993).

HA22-LR-8M Has Excellent Cytotoxic Activity on Cells from CLL Patients

Comparison of the Immunogenicity between PE38 and
New truncated PE, LR8M

A
B
C
D
E
F
Specific IgGs (μg/ml)
OD 450 nm
Folds of dilution
Specific IgG (μg/ml)
Specific IgGs Titer
(days)
17 (Weeks)
n.s.
HA
LR
LR8X
or
LR8M
Immunogen

SEQUENCE LISTING

```
<160> NUMBER OF SEQ ID NOS: 19

<210> SEQ ID NO 1
<211> LENGTH: 613
<212> TYPE: PRT
<213> ORGANISM: Pseudomonas aeruginosa
<220> FEATURE:
<223> OTHER INFORMATION: native Pseudomonas exotoxin A (PE)

<400> SEQUENCE: 1

Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
            20                  25                  30

Ala Ile Ala Asp Thr Asn Gly Gln Gly Val Leu His Tyr Ser Met Val
        35                  40                  45

Leu Glu Gly Gly Asn Asp Ala Leu Lys Leu Ala Ile Asp Asn Ala Leu
    50                  55                  60

Ser Ile Thr Ser Asp Gly Leu Thr Ile Arg Leu Glu Gly Gly Val Glu
65                  70                  75                  80

Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
        115                 120                 125

Met Ser Pro Ile Tyr Thr Ile Glu Met Gly Asp Glu Leu Leu Ala Lys
    130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Thr Gln Pro Arg Arg Glu Lys Arg Trp Ser Glu Trp Ala Ser
            180                 185                 190

Gly Lys Val Leu Cys Leu Leu Asp Pro Leu Asp Gly Val Tyr Asn Tyr
        195                 200                 205
```

-continued

```
Leu Ala Gln Gln Arg Cys Asn Leu Asp Asp Thr Trp Glu Gly Lys Ile
    210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu Gly Gly Ser Leu
                245                 250                 255

Ala Ala Leu Thr Ala His Gln Ala Cys His Leu Pro Leu Glu Thr Phe
            260                 265                 270

Thr Arg His Arg Gln Pro Arg Gly Trp Glu Gln Leu Glu Gln Cys Gly
        275                 280                 285

Tyr Pro Val Gln Arg Leu Val Ala Leu Tyr Leu Ala Ala Arg Leu Ser
    290                 295                 300

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
                325                 330                 335

Arg Leu Ala Leu Thr Leu Ala Ala Ala Glu Ser Glu Arg Phe Val Arg
            340                 345                 350

Gln Gly Thr Gly Asn Asp Glu Ala Gly Ala Ala Asn Ala Asp Val Val
        355                 360                 365

Ser Leu Thr Cys Pro Val Ala Ala Gly Glu Cys Ala Gly Pro Ala Asp
    370                 375                 380

Ser Gly Asp Ala Leu Leu Glu Arg Asn Tyr Pro Thr Gly Ala Glu Phe
385                 390                 395                 400

Leu Gly Asp Gly Gly Asp Val Ser Phe Ser Thr Arg Gly Thr Gln Asn
                405                 410                 415

Trp Thr Val Glu Arg Leu Leu Gln Ala His Arg Gln Leu Glu Glu Arg
            420                 425                 430

Gly Tyr Val Phe Val Gly Tyr His Gly Thr Phe Leu Glu Ala Ala Gln
        435                 440                 445

Ser Ile Val Phe Gly Gly Val Arg Ala Arg Ser Gln Asp Leu Asp Ala
    450                 455                 460

Ile Trp Arg Gly Phe Tyr Ile Ala Gly Asp Pro Ala Leu Ala Tyr Gly
465                 470                 475                 480

Tyr Ala Gln Asp Gln Glu Pro Asp Ala Arg Gly Arg Ile Arg Asn Gly
                485                 490                 495

Ala Leu Leu Arg Val Tyr Val Pro Arg Ser Ser Leu Pro Gly Phe Tyr
            500                 505                 510

Arg Thr Ser Leu Thr Leu Ala Ala Pro Glu Ala Ala Gly Glu Val Glu
        515                 520                 525

Arg Leu Ile Gly His Pro Leu Pro Leu Arg Leu Asp Ala Ile Thr Gly
    530                 535                 540

Pro Glu Glu Glu Gly Gly Arg Leu Glu Thr Ile Leu Gly Trp Pro Leu
545                 550                 555                 560

Ala Glu Arg Thr Val Val Ile Pro Ser Ala Ile Pro Thr Asp Pro Arg
                565                 570                 575

Asn Val Gly Gly Asp Leu Asp Pro Ser Ser Ile Pro Asp Lys Glu Gln
            580                 585                 590

Ala Ile Ser Ala Leu Pro Asp Tyr Ala Ser Gln Pro Gly Lys Pro Pro
        595                 600                 605

Arg Glu Asp Leu Lys
    610
```

-continued

<210> SEQ ID NO 2
<211> LENGTH: 230
<212> TYPE: PRT
<213> ORGANISM: Artificial Sequence
<220> FEATURE:
<223> OTHER INFORMATION: synthetic modified Pseudomonas exotoxin A (PE)
<220> FEATURE:
<221> NAME/KEY: VARIANT
<222> LOCATION: (23)...(209)
<223> OTHER INFORMATION: Xaa = Gly, Ala or Ser

<400> SEQUENCE: 2

```
Arg His Arg Gln Pro Arg Gly Trp Glu Gln Leu Pro Thr Gly Ala Glu
 1               5                  10                  15

Phe Leu Gly Asp Gly Gly Xaa Val Ser Phe Ser Thr Arg Gly Thr Gln
            20                  25                  30

Asn Trp Thr Val Glu Arg Leu Leu Gln Ala His Arg Gln Leu Glu Glu
        35                  40                  45

Xaa Gly Tyr Val Phe Val Gly Tyr His Gly Thr Phe Leu Glu Ala Ala
    50                  55                  60

Gln Ser Ile Val Phe Gly Gly Val Arg Ala Arg Ser Gln Asp Leu Asp
65                  70                  75                  80

Ala Ile Trp Xaa Gly Phe Tyr Ile Ala Gly Asp Pro Ala Leu Ala Tyr
                85                  90                  95

Gly Tyr Ala Gln Asp Gln Glu Pro Asp Ala Xaa Gly Arg Ile Arg Asn
            100                 105                 110

Gly Ala Leu Leu Arg Val Tyr Val Pro Arg Ser Ser Leu Pro Gly Phe
        115                 120                 125

Tyr Xaa Thr Ser Leu Thr Leu Ala Ala Pro Glu Ala Ala Gly Glu Val
    130                 135                 140

Glu Arg Leu Ile Gly His Pro Leu Pro Leu Arg Leu Asp Ala Ile Thr
145                 150                 155                 160

Gly Pro Glu Glu Xaa Gly Gly Arg Leu Glu Thr Ile Leu Gly Trp Pro
                165                 170                 175

Leu Ala Glu Arg Thr Val Val Ile Pro Ser Ala Ile Pro Thr Asp Pro
            180                 185                 190

Arg Asn Val Gly Gly Asp Leu Asp Pro Ser Ser Ile Pro Asp Xaa Glu
        195                 200                 205

Xaa Ala Ile Ser Ala Leu Pro Asp Tyr Ala Ser Gln Pro Gly Lys Pro
    210                 215                 220

Pro Arg Glu Asp Leu Lys
225                 230
```

<210> SEQ ID NO 3
<211> LENGTH: 230
<212> TYPE: PRT
<213> ORGANISM: Artificial Sequence
<220> FEATURE:
<223> OTHER INFORMATION: synthetic modified Pseudomonas exotoxin
      A PE-LR-8M (LR-8M, LR-8X)

<400> SEQUENCE: 3

```
Arg His Arg Gln Pro Arg Gly Trp Glu Gln Leu Pro Thr Gly Ala Glu
 1               5                  10                  15

Phe Leu Gly Asp Gly Gly Ala Val Ser Phe Ser Thr Arg Gly Thr Gln
            20                  25                  30

Asn Trp Thr Val Glu Arg Leu Leu Gln Ala His Arg Gln Leu Glu Glu
        35                  40                  45

Gly Gly Tyr Val Phe Val Gly Tyr His Gly Thr Phe Leu Glu Ala Ala
```

-continued

```
    50                  55                  60

Gln Ser Ile Val Phe Gly Gly Val Arg Ala Arg Ser Gln Asp Leu Asp
65                  70                  75                  80

Ala Ile Trp Ala Gly Phe Tyr Ile Ala Gly Asp Pro Ala Leu Ala Tyr
                85                  90                  95

Gly Tyr Ala Gln Asp Gln Glu Pro Asp Ala Ala Gly Arg Ile Arg Asn
            100                 105                 110

Gly Ala Leu Leu Arg Val Tyr Val Pro Arg Ser Ser Leu Pro Gly Phe
        115                 120                 125

Tyr Ala Thr Ser Leu Thr Leu Ala Ala Pro Glu Ala Ala Gly Glu Val
    130                 135                 140

Glu Arg Leu Ile Gly His Pro Leu Pro Leu Arg Leu Asp Ala Ile Thr
145                 150                 155                 160

Gly Pro Glu Glu Ser Gly Gly Arg Leu Glu Thr Ile Leu Gly Trp Pro
                165                 170                 175

Leu Ala Glu Arg Thr Val Val Ile Pro Ser Ala Ile Pro Thr Asp Pro
            180                 185                 190

Arg Asn Val Gly Gly Asp Leu Asp Pro Ser Ser Ile Pro Asp Ser Glu
        195                 200                 205

Ala Ala Ile Ser Ala Leu Pro Asp Tyr Ala Ser Gln Pro Gly Lys Pro
    210                 215                 220

Pro Arg Glu Asp Leu Lys
225                 230


<210> SEQ ID NO 4
<211> LENGTH: 6
<212> TYPE: PRT
<213> ORGANISM: Artificial Sequence
<220> FEATURE:
<223> OTHER INFORMATION: synthetic variable light chain (VL)
      complementarity determining region CDR1

<400> SEQUENCE: 4

Gln Asp Ile Ser Asn Tyr
 1               5


<210> SEQ ID NO 5
<211> LENGTH: 6
<212> TYPE: PRT
<213> ORGANISM: Artificial Sequence
<220> FEATURE:
<223> OTHER INFORMATION: synthetic variable light chain (VL)
      complementarity determining region CDR1

<400> SEQUENCE: 5

Gln Asp Ile His Gly Tyr
 1               5


<210> SEQ ID NO 6
<211> LENGTH: 6
<212> TYPE: PRT
<213> ORGANISM: Artificial Sequence
<220> FEATURE:
<223> OTHER INFORMATION: synthetic variable light chain (VL)
      complementarity determining region CDR1

<400> SEQUENCE: 6

Gln Asp Ile Gly Arg Tyr
 1               5


<210> SEQ ID NO 7
```

```
<211> LENGTH: 6
<212> TYPE: PRT
<213> ORGANISM: Artificial Sequence
<220> FEATURE:
<223> OTHER INFORMATION: synthetic variable light chain (VL)
      complementarity determining region CDR1

<400> SEQUENCE: 7

Gln Asp Ile Arg Gly Tyr
 1              5


<210> SEQ ID NO 8
<211> LENGTH: 6
<212> TYPE: PRT
<213> ORGANISM: Artificial Sequence
<220> FEATURE:
<223> OTHER INFORMATION: synthetic variable light chain (VL)
      complementarity determining region CDR1

<400> SEQUENCE: 8

Gln Asp Ile Ala Arg Tyr
 1              5


<210> SEQ ID NO 9
<211> LENGTH: 9
<212> TYPE: PRT
<213> ORGANISM: Artificial Sequence
<220> FEATURE:
<223> OTHER INFORMATION: synthetic variable light chain (VL)
      complementarity determining region CDR3

<400> SEQUENCE: 9

Gln Gln Gly Asn Thr Leu Pro Trp Thr
 1              5


<210> SEQ ID NO 10
<211> LENGTH: 8
<212> TYPE: PRT
<213> ORGANISM: Artificial Sequence
<220> FEATURE:
<223> OTHER INFORMATION: synthetic variable heavy chain (VH)
      complementarity determining region CDR1

<400> SEQUENCE: 10

Gly Phe Ala Phe Ser Ile Tyr Asp
 1              5


<210> SEQ ID NO 11
<211> LENGTH: 8
<212> TYPE: PRT
<213> ORGANISM: Artificial Sequence
<220> FEATURE:
<223> OTHER INFORMATION: synthetic variable heavy chain (VH)
      complementarity determining region CDR2

<400> SEQUENCE: 11

Ile Ser Ser Gly Gly Gly Thr Thr
 1              5


<210> SEQ ID NO 12
<211> LENGTH: 16
<212> TYPE: PRT
<213> ORGANISM: Artificial Sequence
<220> FEATURE:
<223> OTHER INFORMATION: synthetic variable heavy chain (VH)
      complementarity determining region CDR3

<400> SEQUENCE: 12
```

```
Ala Arg His Ser Gly Tyr Gly Ser Ser Tyr Gly Val Leu Phe Ala Tyr
 1               5                  10                  15


<210> SEQ ID NO 13
<211> LENGTH: 16
<212> TYPE: PRT
<213> ORGANISM: Artificial Sequence
<220> FEATURE:
<223> OTHER INFORMATION: synthetic variable heavy chain (VH)
      complementarity determining region CDR3

<400> SEQUENCE: 13

Ala Arg His Ser Gly Tyr Gly Thr His Trp Gly Val Leu Phe Ala Tyr
 1               5                  10                  15


<210> SEQ ID NO 14
<211> LENGTH: 16
<212> TYPE: PRT
<213> ORGANISM: Artificial Sequence
<220> FEATURE:
<223> OTHER INFORMATION: synthetic variable heavy chain (VH)
      complementarity determining region CDR3

<400> SEQUENCE: 14

Ala Arg His Ser Gly Tyr Gly Tyr Asn Trp Gly Val Leu Phe Ala Tyr
 1               5                  10                  15


<210> SEQ ID NO 15
<211> LENGTH: 16
<212> TYPE: PRT
<213> ORGANISM: Artificial Sequence
<220> FEATURE:
<223> OTHER INFORMATION: synthetic variable heavy chain (VH)
      complementarity determining region CDR3

<400> SEQUENCE: 15

Ala Arg His Ser Gly Tyr Gly Thr Thr Trp Gly Val Leu Phe Ala Tyr
 1               5                  10                  15


<210> SEQ ID NO 16
<211> LENGTH: 16
<212> TYPE: PRT
<213> ORGANISM: Artificial Sequence
<220> FEATURE:
<223> OTHER INFORMATION: synthetic variable heavy chain (VH)
      complementarity determining region CDR3

<400> SEQUENCE: 16

Ala Arg His Ser Gly Tyr Gly Ser Thr Tyr Gly Val Leu Phe Ala Tyr
 1               5                  10                  15


<210> SEQ ID NO 17
<211> LENGTH: 4
<212> TYPE: PRT
<213> ORGANISM: Artificial Sequence
<220> FEATURE:
<223> OTHER INFORMATION: synthetic C-terminal variant for translocation
      into cytosol

<400> SEQUENCE: 17

Lys Asp Glu Leu
 1


<210> SEQ ID NO 18
<211> LENGTH: 4
<212> TYPE: PRT
<213> ORGANISM: Artificial Sequence
<220> FEATURE:
```

-continued

```
<223> OTHER INFORMATION: synthetic C-terminal variant for translocation
      into cytosol

<400> SEQUENCE: 18

Arg Glu Asp Leu
 1


<210> SEQ ID NO 19
<211> LENGTH: 5
<212> TYPE: PRT
<213> ORGANISM: Artificial Sequence
<220> FEATURE:
<223> OTHER INFORMATION: synthetic native PE C-terminal sequence

<400> SEQUENCE: 19

Arg Glu Asp Leu Lys
 1              5
```

*PSEUDOMONAS* EXOTOXIN A WITH REDUCED IMMUNOGENICITY

CROSS-REFERENCE TO RELATED APPLICATIONS

This present application is the U.S. National Stage entry under §371 of International Application No. PCT/US2010/048504, filed Sep. 10, 2010, which claims the benefit of United States Provisional Patent Application No. 61/241,620, filed Sep. 11, 2009 the contents of which are incorporated by reference herein.

REFERENCE TO A "SEQUENCE LISTING," A TABLE, OR A COMPUTER PROGRAM LISTING APPENDIX SUBMITTED AS AN ASCII TEXT FILE

The Sequence Listing written in file -586-1.TXT, created on Apr. 20, 2012, 16,384 bytes, machine format IBM-PC, MS-Windows operating system, is hereby incorporated by reference in its entirety for all purposes.

FIELD OF THE INVENTION

The present invention provides improved *Pseudomonas* Exotoxin A (PE) molecules with high cytotoxicity and reduced immunogenicity, compositions containing the improved (PE), and methods of use.

BACKGROUND OF THE INVENTION

In the past several years immunoconjugates have been developed as an alternative therapeutic approach to treat malignancies. Immunoconjugates were originally composed of an antibody chemically conjugated to a plant or a bacterial toxin, a form that is known as an immunotoxin. The antibody binds to the antigen expressed on the target cell and the toxin is internalized causing cell death by arresting protein synthesis and inducing apoptosis (Brinkmann, U., *Mol. Med. Today,* 2:439-446 (1996)). More recently, genes encoding the antibody and the toxin have been fused and the immunotoxin expressed as a fusion protein.

A number of studies have been conducted on immunotoxins which use as the toxic moiety a bacterial toxin known as *Pseudomonas* exotoxin A ("PE"). Typically, the PE has been truncated or mutated to reduce its non-specific toxicity without destroying its toxicity to cells to which it is targeted by the targeting portion of the immunotoxin. Clinical trials are currently underway testing the use of PE-based immunotoxins as treatments for a variety of cancers.

Current PE-based immunotoxins are highly immunogenic. This has not proven to be a problem in the treatment of hematological malignancies, in which the ability of the immune system to mount a response is often compromised. Immunotoxins can typically be administered multiple times to patients with hematological malignancies. Patients with solid tumors, however, usually develop neutralizing antibodies to PE-based immunotoxins within weeks after the first administration. Since many protocols call for a three week period between administration of immunotoxins, the development of the antibodies during this period effectively means that, for solid tumors, usually only one administration can be made of a PE-based immunotoxin before the patient's antibodies render it ineffective. Even a single administration of a PE-based immunotoxin can be highly useful in reducing the patient's tumor burden, in eliminating smaller metastases, and in alleviating symptoms. Nonetheless, it would be desirable to have less antigenic forms of PE-based immunotoxins that would reduce patients' immunogenic responses.

The present invention satisfies these and other needs.

BRIEF SUMMARY OF THE INVENTION

The present invention provides improved *Pseudomonas* exotoxin A ("PE") with reduced immunogenicity. Structurally, the improved PE of the invention has Domain I removed, most of Domain II removed, and substitutions within Domain III amino acid residue positions D406, R432, R467, R490, R513, E548, K590 and Q592 with a glycine, alanine or serine. Functionally, the improved PE molecules of the invention retain high cytotoxic activity with the removal of B cell epitopes. Mice receiving 5 injections of the present improved PE did not develop an immune response against the toxin. The improved PE molecules are exemplified by a particular embodiment of the invention referred to here as LR-8M (previously referred to as LR-8X).

Accordingly, in one aspect, the invention provides an isolated *Pseudomonas* exotoxin A ("PE"), wherein said PE has residues 1-273 and 285-394 removed and substitutions of alanine, glycine or serine in place of amino acid residues D406, R432, R467, R490, R513, E548, K590 and Q592 corresponding to an amino acid residue of SEQ ID NO:1.

In a related aspect, the invention provides chimeric molecules comprising (a) a targeting moiety conjugated or fused to (b) a *Pseudomonas* exotoxin A ("PE"), wherein said PE has residues 1-273 and 285-394 removed and substitutions of alanine, glycine or serine in place of amino acid residues D406, R432, R467, R490, R513, E548, K590 and Q592 corresponding to an amino acid residue of SEQ ID NO:1.

In a further aspect, the invention provides compositions comprising (a) a chimeric molecule comprising a targeting moiety conjugated or fused to a *Pseudomonas* exotoxin A ("PE"), wherein said PE has residues 1-273 and 285-394 removed and substitutions of alanine, glycine or serine in place of amino acid residues D406, R432, R467, R490, R513, E548, K590 and Q592 corresponding to an amino acid residue of SEQ ID NO:1, and (b) a pharmaceutically acceptable carrier.

In a related aspect, the invention provides isolated nucleic acids encoding a modified *Pseudomonas* exotoxin A ("PE"), wherein said PE has residues 1-273 and 285-394 removed and substitutions of alanine, glycine or serine in place of amino acid residues D406, R432, R467, R490, R513, E548, K590 and Q592 corresponding to an amino acid residue of SEQ ID NO:1. In some embodiments, the nucleic acid further encodes a targeting moiety.

In another aspect, the invention provides methods of inhibiting the growth of a cell bearing a target molecule, said method comprising contacting said cell with a chimeric molecule comprising (a) a targeting moiety that specifically binds said target molecule, and (b) a *Pseudomonas* exotoxin A ("PE"), wherein said PE has residues 1-273 and 285-394 removed and substitutions of alanine, glycine or serine in place of amino acid residues D406, R432, R467, R490, R513, E548, K590 and Q592 corresponding to an amino acid residue of SEQ ID NO:1, wherein contacting said cell with said chimeric molecule inhibits the growth of said cell.

With respect to the embodiments, in some embodiments, the PE optionally further has a substitution of alanine, glycine or serine of at least one amino acid residue corresponding to an amino acid residue of SEQ ID NO:1 selected from the group consisting of D403, R412, R427, E431, R458, D461, R505, E522, R538, R551, R576 and L597.

In some embodiments, the PE has an amino acid sequence of SEQ ID NO:2. In some embodiments, the PE has an amino acid sequence of SEQ ID NO:3.

In some embodiments, the targeting moiety is an antibody. In some embodiments, the antibody is selected from the group consisting of an scFv, a dsFv, a Fab, a single domain antibody and a $F(ab')_2$.

In some embodiments, the antibody is against a cell surface antigen selected from the group consisting of CD19, CD21, CD22, CD2S, CD30, CD33, CD79b, transferrin receptor, EGF receptor, mesothelin, cadherin and Lewis Y.

In some embodiments, the antibody is selected from the group consisting of B3, RFB4, SS1, HN1, HN2, MN and HB21.

In some embodiments, the antibody has a variable light (VL) chain comprising three complementarity determining regions (CDRs), and a variable heavy (VH) chain comprising three CDRs, wherein (i) said VL CDR1 has the sequence QDIXXY (SEQ ID NOS:4-8), wherein XX is selected from SN, HG, GR, RG and AR;

(ii) said VL CDR2 has the sequence YTS;

(iii) said VL CDR3 has the sequence QQGNTLPWT (SEQ ID NO:9);

(iv) said VH CDR1 has the sequence GFAFSIYD (SEQ ID NO:10);

(v) said VH CDR2 has the sequence ISSGGGTT (SEQ ID NO:11);

(vi) said VH CDR3 has the sequence ARHSGYGXXXGV-LFAY (SEQ ID NOS:12-16), wherein XXX is selected from SSY, THW, YNW, TTW and STY.

In some embodiments, the antibody has a variable light (VL) chain comprising three complementarity determining regions (CDRs), and a variable heavy (VH) chain comprising three CDRs, wherein (i) said VL CDR1 has the sequence QDISNY (SEQ ID NO:4);

(ii) said VL CDR2 has the sequence YTS;

(iii) said VL CDR3 has the sequence QQGNTLPWT (SEQ ID No:9);

(iv) said VH CDR1 has the sequence GFAFSIYD (SEQ ID NO:10);

(v) said VH CDR2 has the sequence ISSGGGTT (SEQ ID NO:11);

(vi) said VH CDR3 has the sequence ARHSGYGTH-WGVLFAY (SEQ ID NO:13).

In some embodiments, the antibody has a variable light (VL) chain comprising three complementarity determining regions (CDRs), and a variable heavy (VH) chain comprising three CDRs, wherein (i) said VL CDR1 has the sequence QDIHGY (SEQ ID NO:5);

(ii) said VL CDR2 has the sequence YTS;

(iii) said VL CDR3 has the sequence QQGNTLPWT (SEQ ID NO:9);

(iv) said VH CDR1 has the sequence GFAFSIYD (SEQ ID NO:10);

(v) said VH CDR2 has the sequence ISSGGGTT (SEQ ID NO:11);

(vi) said VH CDR3 has the sequence ARHSGYGTH-WGVLFAY (SEQ ID NO:13).

In some embodiments, the antibody comprises the Fv portion of HA22. In some embodiments, the antibody is human or humanized.

In some embodiments, the targeting moiety is a cytokine, a lymphokine or a growth factor.

Further embodiments will be apparent to those of ordinary skill and are described herein.

Definitions

Units, prefixes, and symbols are denoted in their Système International de Unites (SI) accepted form. Numeric ranges are inclusive of the numbers defining the range. Unless otherwise indicated, nucleic acids are written left to right in 5' to 3' orientation; amino acid sequences are written left to right in amino to carboxy orientation. The headings provided herein are not limitations of the various aspects or embodiments of the invention, which can be had by reference to the specification as a whole. Accordingly, the terms defined immediately below are more fully defined by reference to the specification in its entirety.

*Pseudomonas* exotoxin A ("PE") is an extremely active monomeric protein (molecular weight 66 kD), secreted by *Pseudomonas aeruginosa*, which inhibits protein synthesis in eukaryotic cells. The native PE sequence (SEQ ID NO.:1) is set forth in U.S. Pat. No. 5,602,095, incorporated herein by reference. The method of action and structure of PE, as well as the modifications resulting in a number of variants of PE, are discussed in some detail in a section devoted to this purpose within.

Mutations of PE are described herein by reference to the amino acid residue present at a particular position of the 613-amino acid sequence of native PE (SEQ ID NO:1), followed by the amino acid with which that residue has been replaced in the particular mutation under discussion. Thus, for example, the term "R490A" indicates that the "R" (arginine, in standard single letter code) at position 490 of the referenced molecule is replaced by an "A" (alanine, in standard single letter code), while "K590Q" indicates that the lysine normally present at position 590 has been replaced with a glutamine. The standard single letter code for common amino acids is set forth below.

"CD22" refers to a lineage-restricted B cell antigen belonging to the Ig superfamily. It is expressed in 60-70% of B cell lymphomas and leukemias and is not present on the cell surface in early stages of B cell development or on stem cells. See, e.g. Vaickus et al., Crit. Rev. Oncol/Hematol. 11:267-297 (1991).

As used herein, the term "anti-CD22" in reference to an antibody that specifically binds CD22 and includes reference to an antibody which is generated against CD22. In preferred embodiments, the CD22 is a primate CD22, such as human CD22. In one preferred embodiment, the antibody is generated against human CD22 synthesized by a non-primate mammal after introduction into the animal of cDNA which encodes human CD22.

"CD25" or "Tac" refers to the alpha chain of the IL-2 receptor (IL2R). It is a type I transmembrane protein present on activated T cells, activated B cells, some thymocytes, myeloid precursors, and oligodendrocytes that associates with CD 122 to form a heterodimer that can act as a high-affinity receptor for IL-2. CD25 expressed in most B-cell neoplasms, some acute nonlymphocytic leukemias, and neuroblastomas.

As used herein, the term "anti-CD25" in reference to an antibody that specifically binds CD25 and includes reference to an antibody which is generated against CD25. In preferred embodiments, the CD25 is a primate CD25, such as human CD25. In one preferred embodiment, the antibody is generated against human CD25 synthesized by a non-primate mammal after introduction into the animal of cDNA which encodes human CD25.

The term "mesothelin" refers to a protein and fragments thereof present on the surface of some human cells and bound by, for example, the K1 antibody. Nucleic acid and amino acid sequences of mesothelin are set forth in, for example, PCT published application WO 97/25,068 and U.S. Pat. Nos. 6,083,502 and 6,153,430. See also, Chang, K. & Pastan, I., *Int. J. Cancer* 57:90 (1994); Chang, K. & Pastan, I., *Proc. Nat'l Acad. Sci. USA* 93:136 (1996); Brinkmann U., et al., *Int. J. Cancer* 71:638 (1997); Chowdhury, P. S., et al., *Mol. Immunol.* 34:9 (1997), and U.S. Pat. No. 6,809,184. Mesothelin is expressed as a precursor protein of approximately 69 kDa, that then is processed to release a 30 kDa protein, while leaving attached to the cell surface the 40 kDa glycosylphosphatidylinositol linked cell surface glycoprotein described in the Background. The 40 kDa glycoprotein is the one referred to by the term "mesothelin" herein. The nucleic acid and amino acid sequences of mesothelin have been recorded from several species, e.g., human (NM_005823.4→NP_005814.2; and NM_013404.3→NP_037536.2), mouse (NM_018857.1→NP_061345.1), rat (NM_031658.1→NP 113846.1), bovine (NM_001100374.1→NP_001093844).

"RFB4" refers to a mouse IgGl monoclonal antibody that specifically binds to human CD22. RFB4 is commercially available under the name RFB4 from several sources, such as Southern Biotechnology Associates, Inc. (Birmingham Ala.; Cat. No. 9360-01), Autogen Bioclear UK Ltd. (Caine, Wilts, UK; Cat. No. AB147), Axxora LLC. (San Diego, Calif.). RFB4 is highly specific for cells of the B lineage and has no detectable cross-reactivity with other normal cell types. Li et al., Cell. Immunol. 118:85-99 (1989). The heavy and light chains of RFB4 have been cloned. See, Mansfield et al., Blood 90:2020-2026 (1997), which is incorporated herein by reference.

"BL22" (or "RFB-4(dsFv)-PE38") is an immunotoxin employing as the targeting moiety a disulfide-stabilized Fv region of the anti-C22 antibody known in the art as "RFB-4". The sequence of the RFB-4 antibody is well known in the art. BL22 is described in Kreitman et al., New Eng J Med 345(4): 241-7 (2001). The BL22 immunotoxin uses PE38 as the toxic portion of the immunotoxin.

"HA22" is an immunotoxin employing as the targeting moiety a mutated form of RFB-4 in which residues SSY of CDR3 of the variable heavy chain have been mutated to THW. This mutation of RFB-4 and its effect on immunotoxins employing it as the targeting moiety are described in International Publication WO 03/027135 and Salvatore et al., Clin Cancer Res 8(4):995-1002 (2002). The HA22 immunotoxin uses PE38 as the toxic portion of the immunotoxin.

For convenience of reference, as used herein, the term "antibody" includes whole (sometimes referred to herein as "intact") antibodies, antibody fragments that retain antigen recognition and binding capability, whether produced by the modification of whole antibodies or synthesized de novo using recombinant DNA methodologies, monoclonal antibodies, polyclonal antibodies, and antibody mimics, unless otherwise required by context. The antibody may be an IgM, IgG (e.g. $IgG_1$, $IgG_2$, $IgG_3$ or $IgG_4$), IgD, IgA or IgE.

Sequences of the constant regions of the IgG subclasses have been well known in the art for years (e.g., Honjo et al., Cell, 18:559-68 (1979); Tucker et al., Science, 206:1303-6 (1979); Yamawaki et al., Nature 283:786-9 (1980); Ellison et al., Nucl Acids Res 10:4071-9 (1982); Ellison et al., DNA 1:11-8 (1981); Ellison and Hood, Proc Natl Acad Sci USA 79:1984-8 (1982)). Since the CDRs of the variable regions determine antibody specificity, CDRs or Fvs of antibodies against a target cell surface antigen can be grafted or engineered into an antibody of choice to confer specificity for the target cell surface antigen upon that antibody. For example, CDRs of an antibody against a target cell surface antigen can be grafted onto a human antibody framework of known three dimensional structure (see, e.g., WO98/45322; WO 87/02671; U.S. Pat. Nos. 5,859,205; 5,585,089; and 4,816,567; EP Patent Application 0173494; Jones, et al. *Nature* 321:522 (1986); Verhoeyen, et al., *Science* 239:1534 (1988), Riechmann, et al. *Nature* 332:323 (1988); and Winter & Milstein, *Nature* 349:293 (1991)) to form an antibody that will raise little or no immunogenic response when administered to a human. Alternatively, the constant regions of the antibodies can be engineered by replacing residues found in non-human animals, such as mice, with residues typically found in humans. Antibodies engineered in this way are referred to as "humanized antibodies" and are preferred, since they have a lower risk of inducing side effects and can remain in the circulation longer. Methods of humanizing antibodies are known in the art and are set forth in, for example, U.S. Pat. Nos. 6,180,377; 6,407,213; 5,693,762; 5,585,089; and 5,530,101.

The term "antibody fragments" means molecules that comprise a portion of an intact antibody, generally the antigen binding or variable region of the intact antibody. Examples of antibody fragments include Fab, Fab', $F(ab')_2$, and Fv fragments; single domain antibodies (see, e.g., Wesolowski, *Med Microbiol Immunol.* (2009) 198(3):157-74; Saerens, et al., *Curr Opin Pharmacol.* (2008) 8(5):600-8; Harmsen and de Haard, *Appl Microbiol Biotechnol.* (2007) 77(1):13-22); helix-stabilized antibodies (see, e.g., Arndt et al., J Mol Biol 312:221-228 (2001); diabodies (see below); single-chain antibody molecules ("scFvs," see, e.g., U.S. Pat. No. 5,888,773); disulfide stabilized antibodies ("dsFvs", see, e.g., U.S. Pat. Nos. 5,747,654 and 6,558,672), and domain antibodies ("dAbs," see, e.g., Holt et al., Trends Biotech 21(11):484-490 (2003), Ghahroudi et al., FEBS Lett. 414:521-526 (1997), Lauwereys et al., EMBO J 17:3512-3520 (1998), Reiter et al., J. Mol. Biol. 290:685-698 (1999), Davies and Riechmann, Biotechnology, 13:475-479 (2001)).

The term "diabodies" refers to small antibody fragments with two antigen-binding sites, which fragments comprise a variable heavy domain ("$V_H$" or "VH") connected to a variable light domain ("$V_L$" or "VL") in the same polypeptide chain ($V_H$-$V_L$). By using a linker that is too short to allow pairing between the two domains on the same chain, the domains are forced to pair with the complementary domains of another chain and create two antigen-binding sites. Diabodies and their production are described more fully in, for example, EP 404,097; WO 93/11161; and Hollinger et al., Proc. Natl. Acad. Sci. USA, 90: 6444-6448 (1993).

The term "parental antibody" means any antibody of interest which is to be mutated or varied to obtain antibodies or fragments thereof which bind to the same epitope as the parental antibody, but with higher affinity.

A "targeting moiety" is the portion of an immunoconjugate intended to target the immunoconjugate to a cell of interest. Typically, the targeting moiety is an antibody, or a fragment of an antibody that retains antigen recognition capability, such as a scFv, a dsFv, an Fab, or an $F(ab')_2$.

A "toxic moiety" is the portion of a immunotoxin which renders the immunotoxin cytotoxic to cells of interest. With regard to the immunotoxins which are the subject of the present invention, the toxic moiety is a *Pseudomonas* exotoxin A which has been mutated to reduce its non-specific cytotoxicity, as described in some detail below.

Typically, an immunoglobulin has a heavy and light chain. Each heavy and light chain contains a constant region and a variable region, (the regions are also known as "domains"). Light and heavy chain variable regions contain a "framework" region interrupted by three hypervariable regions, also called "complementarity-determining regions" or "CDRs". The extent of the framework region and CDRs have been defined. The sequences of the framework regions of different light or heavy chains are relatively conserved within a species. The framework region of an antibody, that is the combined framework regions of the constituent light and heavy chains, serves to position and align the CDRs in three dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found.

References to "$V_H$" or a "VH" refer to the variable region of an immunoglobulin heavy chain, including an Fv, scFv , dsFv or Fab. References to "$V_L$" or a "VL" refer to the variable region of an immunoglobulin light chain, including of an Fv, scFv , dsFv or Fab The phrase "single chain Fv" or "scFv" refers to an antibody in which the variable domains of the heavy chain and of the light chain of a traditional two chain antibody have been joined to form one chain. Typically, a linker peptide is inserted between the two chains to allow for proper folding and creation of an active binding site.

The phrase "disulfide bond" or "cysteine-cysteine disulfide bond" refers to a covalent interaction between two cysteines in which the sulfur atoms of the cysteines are oxidized to form a disulfide bond. The average bond energy of a disulfide bond is about 60 kcal/mol compared to 1-2 kcal/mol for a hydrogen bond.

The phrase "disulfide stabilized Fv" or "dsFv" refer to the variable region of an immunoglobulin in which there is a disulfide bond between the light chain and the heavy chain. In the context of this invention, the cysteines which form the disulfide bond are within the framework regions of the antibody chains and serve to stabilize the conformation of the antibody. Typically, the antibody is engineered to introduce cysteines in the framework region at positions where the substitution will not interfere with antigen binding.

The term "linker peptide" includes reference to a peptide within an antibody binding fragment (e.g., Fv fragment) which serves to indirectly bond the variable domain of the heavy chain to the variable domain of the light chain.

An antibody immunologically reactive with a particular antigen can be generated by recombinant methods such as selection of libraries of recombinant antibodies in phage or similar vectors, see, e.g., Huse, et al., *Science* 246:1275-1281 (1989); Ward, et al., *Nature* 341:544-546 (1989); and Vaughan, et al., *Nature Biotech.* 14:309-314 (1996), or by immunizing an animal with the antigen or with DNA encoding the antigen.

The term "effector moiety" means the portion of an immunoconjugate intended to have an effect on a cell targeted by the targeting moiety or to identify the presence of the immunoconjugate. In the context of the present invention, the effector moiety is a mutated *Pseudomonas* exotoxin A.

The term "immunoconjugate" includes reference to a covalent linkage of an effector molecule to an antibody.

The terms "effective amount" or "amount effective to" or "therapeutically effective amount" includes reference to a dosage of a therapeutic agent sufficient to produce a desired result, such as inhibiting cell protein synthesis by at least 50%, or killing the cell.

The term "toxin" typically includes reference to abrin, ricin, *Pseudomonas* exotoxin (PE), diphtheria toxin (DT), botulinum toxin, or modified toxins thereof. For example, PE and DT are highly toxic compounds that typically bring about death through liver toxicity. PE and DT, however, can be modified into a form for use as an immunotoxin by removing the native targeting component of the toxin (e.g., domain Ia of PE or the B chain of DT) and replacing it with a different targeting moiety, such as an antibody. In the context of the present invention, the toxin is a mutated *Pseudomonas* exotoxin A.

The term "contacting" includes reference to placement in direct physical association.

An "expression plasmid" comprises a nucleotide sequence encoding a molecule or interest, which is operably linked to a promoter.

As used herein, "polypeptide", "peptide" and "protein" are used interchangeably and include reference to a polymer of amino acid residues. The terms apply to amino acid polymers in which one or more amino acid residue is an artificial chemical analogue of a corresponding naturally occurring amino acid, as well as to naturally occurring amino acid polymers. The terms also apply to polymers containing conservative amino acid substitutions such that the protein remains functional.

The term "residue" or "amino acid residue" or "amino acid" includes reference to an amino acid that is incorporated into a protein, polypeptide, or peptide (collectively "peptide"). The amino acid can be a naturally occurring amino acid and, unless otherwise limited, can encompass known analogs of natural amino acids that can function in a similar manner as naturally occurring amino acids.

The amino acids and analogs referred to herein are described by shorthand designations as follows in Table A:

TABLE A

Amino Acid Nomenclature

| Name | 3-letter | 1-letter |
|---|---|---|
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Homoserine | Hse | — |
| Isoleucine | Ile | I |
| Leucine | Leu | L |
| Lysine | Lys | K |
| Methionine | Met | M |
| Methionine sulfoxide | Met (O) | — |
| Methionine methylsulfonium | Met (S—Me) | — |
| Norleucine | Nle | — |
| Phenylalanine | Phe | F |
| Proline | Pro | P |
| Serine | Ser | S |
| Threonine | Thr | T |
| Tryptophan | Trp | W |

TABLE A-continued

| Amino Acid Nomenclature | | |
|---|---|---|
| Name | 3-letter | 1-letter |
| Tyrosine | Tyr | Y |
| Valine | Val | V |

A "conservative substitution", when describing a protein refers to a change in the amino acid composition of the protein that does not substantially alter the protein's activity. Thus, "conservatively modified variations" of a particular amino acid sequence refers to amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well known in the art. The following six groups in Table B each contain amino acids that are conservative substitutions for one another:

TABLE B

| |
|---|
| 1) Alanine (A), Serine (S), Threonine (T); |
| 2) Aspartic acid (D), Glutamic acid (E); |
| 3) Asparagine (N), Glutamine (Q); |
| 4) Arginine (R), Lysine (K); |
| 5) Isoleucine (I), Leucine (L), Methionine (M), Valine (V); and |
| 6) Phenylalanine (F), Tyrosine (Y), Tryptophan (W). |

See also, Creighton, *Proteins: Structures and Molecular Properties*, W.H. Freeman and Company, New York (2nd Ed., 1992).

The terms "substantially similar" in the context of a peptide indicates that a peptide comprises a sequence with at least 90%, preferably at least 95% sequence identity to the reference sequence over a comparison window of 10-20 amino acids. Percentage of sequence identity is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "conjugating," "joining," "bonding" or "linking" refer to making two polypeptides into one contiguous polypeptide molecule. In the context of the present invention, the terms include reference to joining an antibody moiety to an effector molecule (EM). The linkage can be either by chemical or recombinant means. Chemical means refers to a reaction between the antibody moiety and the effector molecule such that there is a covalent bond formed between the two molecules to form one molecule.

As used herein, "recombinant" includes reference to a protein produced using cells that do not have, in their native state, an endogenous copy of the DNA able to express the protein. The cells produce the recombinant protein because they have been genetically altered by the introduction of the appropriate isolated nucleic acid sequence. The term also includes reference to a cell, or nucleic acid, or vector, that has been modified by the introduction of a heterologous nucleic acid or the alteration of a native nucleic acid to a form not native to that cell, or that the cell is derived from a cell so modified. Thus, for example, recombinant cells express genes that are not found within the native (non-recombinant) form of the cell, express mutants of genes that are found within the native form, or express native genes that are otherwise abnormally expressed, underexpressed or not expressed at all.

As used herein, "nucleic acid" or "nucleic acid sequence" includes reference to a deoxyribonucleotide or ribonucleotide polymer in either single- or double-stranded form, and unless otherwise limited, encompasses known analogues of natural nucleotides that hybridize to nucleic acids in a manner similar to naturally occurring nucleotides. Unless otherwise indicated, a particular nucleic acid sequence includes the complementary sequence thereof as well as conservative variants, i.e., nucleic acids present in wobble positions of codons and variants that, when translated into a protein, result in a conservative substitution of an amino acid.

As used herein, "encoding" with respect to a specified nucleic acid, includes reference to nucleic acids which comprise the information for translation into the specified protein. The information is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolum* (*Proc. Nat'l Acad. Sci. USA* 82:2306-2309 (1985), or the ciliate *Macronucleus*, may be used when the nucleic acid is expressed in using the translational machinery of these organisms.

The phrase "fusing in frame" refers to joining two or more nucleic acid sequences which encode polypeptides so that the joined nucleic acid sequence translates into a single chain protein which comprises the original polypeptide chains.

As used herein, "expressed" includes reference to translation of a nucleic acid into a protein. Proteins may be expressed and remain intracellular, become a component of the cell surface membrane or be secreted into the extracellular matrix or medium.

By "host cell" is meant a cell which can support the replication or expression of the expression vector. Host cells may be prokaryotic cells such as *E. coli*, or eukaryotic cells such as yeast, insect, amphibian, or mammalian cells.

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least 60%, more preferably 65%, even more preferably 70%, still more preferably 75%, even more preferably 80%, and most preferably 90-95% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. AppL Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology,* F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) *J. Mol. Biol.* 215: 403-410 and Altschuel et al. (1977) *Nucleic Acids Res.* 25: 3389-3402, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

The term "in vivo" includes reference to inside the body of the organism from which the cell was obtained. "Ex vivo" and "in vitro" means outside the body of the organism from which the cell was obtained.

The phrase "malignant cell" or "malignancy" refers to tumors or tumor cells that are invasive and/or able to undergo metastasis, i.e., a cancerous cell.

As used herein, "mammalian cells" includes reference to cells derived from mammals including humans, rats, mice, guinea pigs, chimpanzees, or macaques. The cells may be cultured in vivo or in vitro.

The term "selectively reactive" refers, with respect to an antigen, the preferential association of an antibody, in whole or part, with a cell or tissue bearing that antigen and not to cells or tissues lacking that antigen. It is, of course, recognized that a certain degree of non-specific interaction may occur between a molecule and a non-target cell or tissue. Nevertheless, selective reactivity, may be distinguished as mediated through specific recognition of the antigen. Although selectively reactive antibodies bind antigen, they may do so with low affinity. On the other hand, specific binding results in a much stronger association between the antibody and cells bearing the antigen than between the bound antibody and cells lacking the antigen. Specific binding typically results in greater than 2-fold, preferably greater than 5-fold, more preferably greater than 10-fold and most preferably greater than 100-fold increase in amount of bound antibody (per unit time) to a cell or tissue bearing the target antigen as compared to a cell or tissue lacking the target antigen. Specific binding to a protein under such conditions requires an antibody that is selected for its specificity for a particular protein. A variety of immunoassay formats are appropriate for selecting antibodies specifically immunoreactive with a particular protein. For example, solid-phase ELISA immunoassays are routinely used to select monoclonal antibodies specifically immunoreactive with a protein. See Harlow & Lane, Antibodies, A Laboratory Manual, Cold Spring Harbor Publications, New York (1988), for a description of immunoassay formats and conditions that can be used to determine specific immunoreactivity.

The term "immunologically reactive conditions" includes reference to conditions which allow an antibody generated to a particular epitope to bind to that epitope to a detectably greater degree than, and/or to the substantial exclusion of, binding to substantially all other epitopes. Immunologically reactive conditions are dependent upon the format of the antibody binding reaction and typically are those utilized in immunoassay protocols or those conditions encountered in vivo. See Harlow & Lane, supra, for a description of immunoassay formats and conditions. Preferably, the immunologically reactive conditions employed in the methods of the present invention are "physiological conditions" which include reference to conditions (e.g., temperature, osmolarity, pH) that are typical inside a living mammal or a mammalian cell. While it is recognized that some organs are subject to extreme conditions, the intra-organismal and intracellular environment normally lies around pH 7 (i.e., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

The terms "patient," "subject," "individual" interchangeably refer to a mammal, for example, a human or a non-human primate, a domesticated mammal (e.g., a canine or feline), an agricultural mammal (e.g., a bovine, porcine, ovine, equine), a laboratory mammal (a mouse, rat, hamster, rabbit).

The term "co-administer" refers to the simultaneous presence of two active agents in the blood of an individual. Active agents that are co-administered can be concurrently or sequentially delivered.

As used herein, the terms "treating" and "treatment" refer to delaying the onset of, retarding or reversing the progress of, or alleviating or preventing either the disease or condition to which the term applies, or one or more symptoms of such disease or condition.

The terms "inhibiting," "reducing," "decreasing" with respect to tumor or cancer growth or progression refers to inhibiting the growth, spread, metastasis of a tumor or cancer in a subject by a measurable amount using any method known in the art. The growth, progression or spread of a tumor or cancer is inhibited, reduced or decreased if the tumor burden is at least about 10%, 20%, 30%, 50%, 80%, or 100% reduced in comparison to the tumor burden prior to the co-administration of a PE of the present invention, e.g., as part of a chimeric molecule. In some embodiments, the growth, progression or spread of a tumor or cancer is inhibited, reduced or decreased by at least about 1-fold, 2-fold, 3-fold, 4-fold, or more in comparison to the tumor burden prior to administration of the PE.

DETAILED DESCRIPTION

1. Introduction

Figure 1:
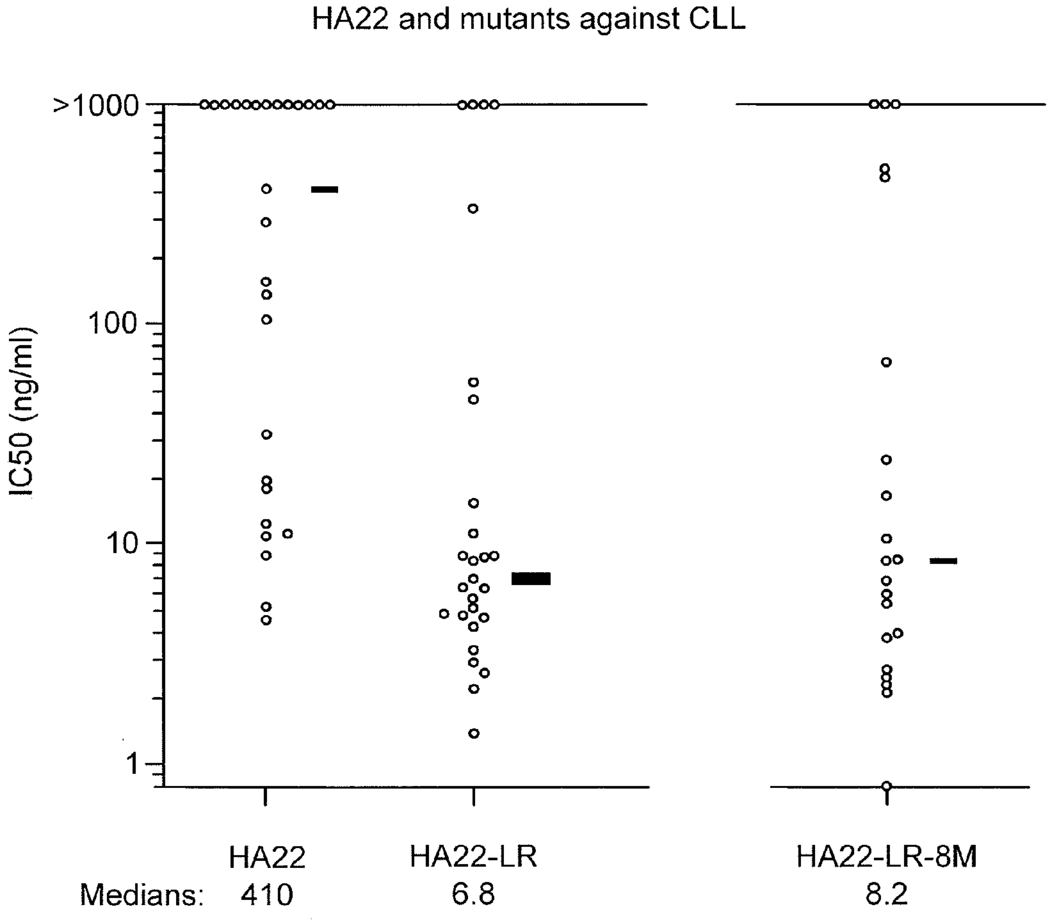
FIG. 1 illustrates that HA22-LR-8M has excellent cell killing activity against chronic lymphatic leukemia (CLL) cells from CLL patients.

For over 15 years, *Pseudomonas* exotoxin A ("PE") has been investigated for use as the toxic portion of chimeric molecules such as immunotoxins. That work is embodied in the development of a number of mutated forms of PE in which cytotoxic activity has been retained, while non-specific toxicity of the molecule has been reduced or eliminated. Most of these mutants have been truncated to improve their tumor penetration. Some have also had modifications in addition to truncation, such as modifying the carboxyl terminal residues or eliminating the requirement for cleavage between residues 279 and 280 by the protease furin, to increase their cytotoxicity. Immunotoxins using mutated forms of PE have shown considerable therapeutic promise in human clinical trials.

The use of PE-based immunotoxins for treatment of solid tumors in particular, however, has been limited because of the development of neutralizing antibodies to the immunotoxin after the first administration. These antibodies develop before most protocols would call for a second administration of the immunotoxin, and therefore render further use of the immunotoxins ineffective against solid tumors in previously exposed patients.

The studies underlying the present invention reveal that the predominant immune response of patients to PE-based immunotoxins is to the PE portion of the immunotoxin. This understanding indicates that reducing the antigenicity of the PE molecules used for immunotoxins would reduce the overall antigenicity of the immunotoxin, and increase their utility. The studies underlying the present invention further reveal that PE has seven major epitopes, which can be further divided into a total of thirteen subepitopes.

Surprisingly, it has been discovered that, for ten of the thirteen subepitopes of PE, the antigenicity of the epitope or subepitope can be reduced or eliminated by mutating a single amino acid residue of PE. Of course, since PE contains a multiplicity of antigenic epitopes, no single mutation eliminates the antigenicity of the whole PE molecule. Each individual mutation of the present invention, however, reduces the antigenicity of an individual epitope or subepitope. The individual mutations therefore reduce the antigenicity of the overall PE molecule and any immunotoxin made with the mutated PE.

The studies underlying the invention have further demonstrated that various of the mutations can be combined to reduce the overall antigenicity of the molecule while retaining the cytotoxicity of the PE molecule. PE molecules were made in which 8 amino acid residues of different epitopes or subepitopes, including residues D406 and Q592, were mutated. The PEs with the mutations were made into immunotoxins, and their cytotoxicity assayed. For ease of comparison, the PEs were made into immunotoxins each of which used the same targeting moiety (a high affinity, anti-CD22 antibody). Further, to facilitate comparison, the PE38 form of PE was used as the PE in which the substitutions were made. Given our experience with many PE-based immunotoxins over the past 15 years, the fact that all cytotoxic forms of PE share the same mechanism of cytotoxicity to target cells (ADP-ribosylation of elongation factor 2), and the fact that the other variants of PE in use are simply the same amino acid sequence with particular truncations (or, in the case of PE4E, four mutations in domain la, rather than a truncation), the results obtained with PE38 are expected to be directly applicable to other forms of PE (such as the exemplar forms known respectively as PE25, PE40, PE38, PE37, PE35, PE4E, PE38QQR, and PE38KDEL).

It is expected that, as immunotoxins, the mutated PEs already made, and others modified according to the teachings of the present invention, will, when made into immunotoxins, provoke less of an immune response in vivo, and that this lessened immune response will be reflected by lower titers of neutralizing antibodies. The development of neutralizing antibodies is routinely assayed in preclinical testing of immunotoxins and in immunotoxin clinical trial protocols, and the antibody titers induced by immunotoxins made using the PEs of the invention can be measured by these standard assays.

Persons of skill will appreciate that the PEs of the invention will be as useful as the mutated PEs previously known which have been made into immunotoxins and tested in clinical trials. As noted, however, immunotoxins made with the PEs of the invention are expected to display less antigenicity than do immunotoxins made with currently available PE molecules, and to thereby provoke less of an immune response in patients than do currently available PE-based immunotoxins.

The mutations of the present invention can be easily engineered into already-modified PEs (such as the exemplar forms known respectively as PE25, PE40, PE38, PE37, PE35, PE4E, PE38QQR, and PE38KDEL) to reduce their antigenicity, and thereby reduce patients' immunogenic responses to immunotoxins containing them. Accordingly, the invention provides an important new means of increasing the therapeutic utility of PE-based immunoconjugates, such as the various PE-based immunotoxins currently in clinical trials.

As noted, the improved PEs of the invention comprise mutations of the molecule at specific positions of the PE molecule. By convention, positions in PE and its variants are notated in the art by reference to the corresponding position in the 613 amino acid sequence of the native PE molecule (SEQ ID NO:1). This convention is followed herein to permit ready comparison among PE variants and to promote understanding which residues are mutated in the PEs of the invention. For example, as discussed in more detail below, in most clinically useful forms of PE, domain Ia (amino acids 1-252) of the molecule is deleted to reduce non-specific binding. A PE with domain Ia deleted has only 361 residues. Nonetheless, a reference herein to D406 refers to the aspartate found at position 406 of the native PE sequence, regardless of the number of that residue if counted from the amino terminus of the particular PE in which it occurs, while R590 refers to the lysine found at position 590 of native PE and so on. The amino acid sequence of native PE (SEQ ID NO.:1) is well known in the art and is set forth, for example, in U.S. Pat. No. 5,602,095.

As indicated below, in preferred embodiments, in the compositions and methods of the invention, the amino acid residue present in the native sequence of PE at the positions identified herein is replaced by an amino acid selected from the group alanine, glycine or serine. Alanine, glycine and serine are particularly preferred as the replacement residues, with alanine and serine being particularly preferred.

To be useful, the PE must retain cytotoxic activity following the substitutions of the residues. To test the retention of cytotoxicity by PEs altered to reduce their antigenicity, a number of exemplar immunotoxins have been made. In a first series of studies, nineteen immunotoxins were made. To permit comparison, each of these immunotoxins used the same targeting moiety and each started with the same truncated form of PE known as PE38. In each of the nineteen immunotoxins, a different residue of PE38 was replaced by a mutation identified as reducing the antigenicity of a particular PE epitope or subepitope. The cytotoxic activity of these nineteen mutated PE38s was then compared to an immunotoxin made with the same targeting moiety and with unaltered PE38 (which for convenience will be called the "wild type" immunotoxin). Variants of PE with reduced antigenicity are described, e.g., in PCT Appl. No. PCT/US06/28986 (Published as WO 2007/016150).

The studies underlying the invention revealed amino acids whose replacement decreased at least 5-fold, more preferably at least 10-fold, and most preferably at least 20-fold, the binding to more than two monoclonal antibodies ("MAbs") assigned to the same epitope. It is expected that the reduction of binding of MAbs to the epitope correlates with a loss of antigenicity of the epitope, and therefore of PE molecules containing the mutation.

In WO 2007/016150, mutations found to reduce binding of MAbs to the same epitope by at least 5-fold were E282, E285, P290, R313, N314, P319, D324, E327, E331, Q332, D403, R412, R427, E431, R432, R458, D461, R467, R490, R505, R513, E522, R538, E548, R551, R576, K590, and L597. The positions of PE at which mutations were found to reduce binding of MAbs to the same epitope by at least 10-fold were E282, E285, P290, R313, N314, D324, E327, E331, Q332, D403, R412, E431, R427, R432, R458, D461, R467, R490, R505, R513, E522, R538, E548, R576, and R590. The positions of PE at which mutations were found to reduce binding of MAbs to the same epitope by at least 20-fold were N314, D324, E327, E331, Q332, D403, R432, R467, R490, R505, R513, R538, R551, K590, and L597.

In previous studies by the laboratory of the present inventors, reported in PCT application PCT/US2004/039617 (International Publication WO 2005/052006), it was discovered that mutating PE residue R490 to alanine doubled the cytotoxicity of the resulting PE molecule when used as the toxin moiety of an immunotoxin. Surprisingly, the studies underlying the present invention show that mutation of the arginine at PE position 490 also eliminates antibody binding to PE epitope 5. Therefore, replacement of the arginine at position 490 of PE with one of the residues discussed above is expected to decrease the antigenicity of the PE molecule. It is further expected that combining replacement of the arginine at PE position 490 with the replacement of one or more residues that reduce binding to one of the epitopes or subepitopes of PE other than epitope 5 will further reduce the antigenicity of the molecule and the development of antibodies to the PE portion of an immunotoxin made with the resulting PE. It is noted that no mutations were found that reduced binding to subepitope 2a.

WO 2005/052006 further indicates that the arginine at position 490 of PE can be mutated to glycine, alanine, valine, leucine, or isoleucine. Increased cytotoxic activity and decreased immunogenicity are separate phenomena. Therefore, not all mutations that are expected to result in increased cytotoxic activity are also expected to result in decreased immunogenicity. Mutations that do both, such as mutations of R490 to glycine or, more preferably, alanine, are particularly desirable.

Surprisingly, it has now been discovered that certain other residues, namely D406 and Q592, can be mutated and also result in PEs which can be made into immunotoxins with high cytotoxicity and reduced antigenicity.

Persons of skill are aware that various types of molecules can serve as a basis of targeting PEs containing the mutations of the invention to cells that the practitioner wishes to kill or to inhibit. As evident from the discussion above, antibodies are one especially preferred type of targeting agent.

In another preferred embodiment, the targeting portion, or moiety, of the chimeric molecule is a cytokine, which can be used to target toxins to cells overexpressing a receptor for the cytokine. IL-13 receptors, for example, are known to be heavily overexpressed on the exterior of cells of certain cancers, such as gliomas, and to act as an autocrine growth factor on such cancers as renal cell carcinoma, Kaposi's sarcoma, and Hodgkin's disease. See, e.g., WO 01/34645, WO 03/039600 and U.S. Pat. No. 6,518,061. IL-13 or various mutants and circularly permuted forms of IL-13 can be used to target cytotoxins, such as PE molecules containing one or more mutations of the invention to cells expressing the IL-13 receptor. Further, the various forms of IL-13, including circularly permuted forms, can be used to target PE molecules with the mutations to cells in the lungs expressing IL-13 receptor to reduce or end symptoms in conditions, such as asthma and allergic rhinitis, and to cells elsewhere in the body to reduce or end symptoms of atopic dermatitis, and hepatic fibrosis in schistosomiasis, as discussed in international publication WO 01/34645.

In addition to cytokines, numerous other ligands are known in the art and can be used for targeting PE molecules of the invention to target cells. For example, transferrin has been used as a means of targeting toxins to cells expressing transferrin receptors. Similarly, cells involved in a disease or condition can be targeted if there is an antigen on the cell surface that is specifically or preferentially expressed in cells related to the disease or condition, such as gp120 in HIV-infected cells, CD25 on T cells that are involved in graft versus host disease or various surface molecules that are expressed on cancer cells, such as CEA, CD30, or CD33.

2. Improved PE Molecules with Reduced Antigenicity

Native *Pseudomonas* exotoxin A ("PE") is an extremely active monomeric protein (molecular weight 66 kD), secreted by *Pseudomonas aeruginosa*, which inhibits protein synthesis in eukaryotic cells. The native PE sequence is set forth in SEQ ID NO:1 of U.S. Pat. No. 5,602,095, incorporated herein by reference. The method of action is inactivation of the ADP-ribosylation of elongation factor 2 (EF-2). The exotoxin contains three structural domains that act in concert to cause cytotoxicity. Domain la (amino acids 1-252) mediates cell binding. Domain II (amino acids 253-364) is responsible for translocation into the cytosol and domain III (amino acids 400-613) mediates ADP ribosylation of elongation factor 2. The function of domain Ib (amino acids 365-399) remains undefined, although a large part of it, amino acids 365-380, can be deleted without loss of cytotoxicity. See Siegall, et al., J Biol Chem 264:14256-61 (1989).

The terms "*Pseudomonas* exotoxin" and "PE" as used herein typically refer to a PE that has been modified from the native protein to reduce or to eliminate non-specific toxicity. Numerous such modifications are known in the art and include, but are not limited to, elimination of domain Ia, various amin6o acid deletions in domains Ib, II and III, single amino acid substitutions and the addition of one or more sequences at the carboxyl terminus such as KDEL (SEQ ID NO:17) and REDL (SEQ ID NO:18). See Siegall, et al., J Biol. Chem. 264:14256-14261 (1989). Cytotoxic fragments of PE include those which are cytotoxic with or without subsequent proteolytic or other processing in the target cell (e.g., as a protein or pre-protein). Cytotoxic fragments of PE include PE40, PE38 and its variants PE38QQR and PE38KDEL (in which PE38 has the sequence KDEL (SEQ ID NO:17) added at the C-terminus), and PE35, as discussed below. In a preferred embodiment, the cytotoxic fragment of PE retains at least about 20%, preferably at least about 40%, more preferably about 50%, even more preferably 75%, more preferably at least about 90%, and still more preferably 95% of the cytotoxicity of native PE. In particularly preferred embodiments, the cytotoxic fragment has at least the cytotoxicity of native PE, and preferably has more.

In preferred embodiments, the PE has been modified to reduce or eliminate non-specific cell binding, frequently by deleting domain Ia. as taught in U.S. Pat. No. 4,892,827, although this can also be achieved, for example, by mutating certain residues of domain Ia. U.S. Pat. No. 5,512,658, for instance, discloses that a mutated PE in which Domain Ia is present but in which the basic residues of domain Ia at positions 57, 246, 247, and 249 are replaced with acidic residues (glutamic acid, or "E")) exhibits greatly diminished non-specific cytotoxicity. This mutant form of PE is sometimes referred to as "PE4E."

PE40 is a truncated derivative of PE previously described in the art. See, Pai, et al., *Proc. Nat'l Acad. Sci. USA* 88:3358-62 (1991); and Kondo, et al., *J. Biol. Chem.* 263:9470-9475 (1988). PE35 is a 35 kD carboxyl-terminal fragment of PE in which amino acid residues 1-279 have deleted and the molecule commences with a met at position 280 followed by amino acids 281-364 and 381-613 of native PE. PE35 and PE40 are disclosed, for example, in U.S. Pat. Nos. 5,602,095 and 4,892,827. Another derivative is PE25, containing the 11-residue fragment from domain II and all of domain III. In some embodiments, the derivative of PE contain only domain III.

In some preferred embodiments, the cytotoxic fragment PE38 is employed. PE38 contains the translocating and ADP ribosylating domains of PE but not the cell-binding portion (Hwang, J. et al., *Cell,* 48:129-136 (1987)). PE38 is a truncated PE pro-protein composed of amino acids 253-364 and 381-613 which is activated to its cytotoxic form upon processing within a cell (see e.g., U.S. Pat. No. 5,608,039, and Pastan et al., Biochim. Biophys. Acta 1333:C1-C6 (1997)). The sequence of PE38 is therefore known in the art, but could also readily be determined by the practitioner by subtracting the stated residues from the known sequence of PE. Persons of skill will be aware that, due to the degeneracy of the genetic code, the amino acid sequence of PE38, of its variants, such as PE38KDEL, and of the other PE derivatives discussed herein can be encoded by a great variety of nucleic acid sequences, any of which can be expressed to result in the desired polypeptide.

As noted above, some or all of domain 1b may be deleted, and the remaining portions joined by a linker or directly by a peptide bond. Some of the amino portion of domain II may be deleted. And, the C-terminal end may contain the native sequence of residues 609-613 (REDLK; SEQ ID NO:19), or may contain a variation found to maintain the ability of the construct to translocate into the cytosol, such as KDEL (SEQ ID NO:17) or REDL (SEQ ID NO:18), and repeats of these sequences. See, e.g., U.S. Pat. Nos. 5,854,044; 5,821,238; and 5,602,095 and WO 99/51643. While in preferred embodiments, the PE is PE4E, PE40, or PE38, any form of PE in which non-specific cytotoxicity has been eliminated or reduced to levels in which significant toxicity to non-targeted cells does not occur can be used in the immunotoxins of the present invention so long as it remains capable of translocation and EF-2 ribosylation in a targeted cell.

In preferred embodiments, the PE molecules are modified to have a substitution of alanine, glycine, serine or glutamine in place of the amino acid residues normally present at positions D406 and Q592 within Domain III. Substitutions at positions D406 and Q592 can be combined with substitutions of alanine, glycine, serine or glutamine at positions R432, R467, R490, R513, E548 and K590 within Domain III. In some embodiments, in addition, at least one amino acid residue corresponding to an amino acid residue at a position selected from D403, R412, R427, E431, R458, D461, R505, E522, R538, R551, 8576 and L597 is substituted with an alanine, glycine, serine or glutamine. The substitutions to the residues at positions substitutions within Domain III amino acid residue positions D406, R432, R467, R490, R513, E548, K590 and Q592 of Domain III are preferably combined with the removal of all of Domain Ia (e.g., residues 1-252) and the removal of most of Domain II (e.g. residues 251-273 and 285-394). In some embodiments, the PE has an amino acid sequence of SEQ ID NO:2. In some embodiments, the PE has an amino acid sequence of SEQ ID NO:3.

A. Conservatively Modified Variants of PE

It is understood that the sequence of native PE and the variants discussed above can have conservative substitutions and retain cytotoxic capability and, desirably, reduced antigenicity compared to the native sequence of PE. In preferred embodiments, modified variants of PE or cytotoxic fragments thereof have at least 80% sequence similarity, preferably at least 85% sequence similarity, more preferably at least 90% sequence similarity, and most preferably at least 95% sequence similarity at the amino acid level, with the PE of interest, such as PE38.

The term "conservatively modified variants" applies to both amino acid and nucleic acid sequences. With respect to particular nucleic acid sequences, conservatively modified variants refer to those nucleic acid sequences which encode identical or essentially identical amino acid sequences, or if the nucleic acid does not encode an amino acid sequence, to essentially identical nucleic acid sequences. Because of the degeneracy of the genetic code, a large number of functionally identical nucleic acids encode any given polypeptide. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid.

B. Assaying for Cytotoxicity or Antigenicity of PE

*Pseudomonas* exotoxins employed in the invention can be assayed for the desired level of cytotoxicity by assays well known to those of skill in the art. Thus, cytotoxic fragments of PE and conservatively modified variants of such fragments can be readily assayed for cytotoxicity. A large number of candidate PE molecules can be assayed simultaneously for cytotoxicity by methods well known in the art. For example, subgroups of the candidate molecules can be assayed for cytotoxicity. Positively reacting subgroups of the candidate molecules can be continually subdivided and reassayed until the desired cytotoxic fragment(s) is identified. Such methods allow rapid screening of large numbers of cytotoxic fragments or conservative variants of PE. Antigenicity can be assayed any method known in the art, including the assays taught in WO 2007/016150.

Preferred PE variants exhibit equivalent or greater cytotoxicity, e.g., in comparison to an unsubstituted PE, e.g., PE38. While more cytotoxicity is usually preferable to less, in practice the reduced cytotoxicity of these mutated forms of PE is expected to be offset to at least some degree by the reduced antigenicity of the PE and the immunotoxins made with them. Thus, even these PEs with reduced cytotoxicity find use. Moreover, coupled with a PE mutation that exhibits increased cytotoxicity when made into an immunotoxin, the cytotoxicity of the PE may be closer to that of the wild type PE. And, since PE is a very potent cytotoxin, even mutated forms of PE with toxicity considerably reduced from that of the native toxin retain considerable power as toxic moieties.

3. Chimeric Molecules

Immunoconjugates of the invention include, but are not limited to, molecules in which there is a covalent linkage of a PE molecule to an antibody or other targeting agent. The choice of a particular targeting agent depends on the particular cell to be targeted. With the PE molecules provided herein, one of skill can readily construct a variety of clones containing functionally equivalent nucleic acids, such as nucleic acids which differ in sequence but which encode the same PE and antibody sequence. Thus, the present invention provides nucleic acids encoding antibodies and PE conjugates and fusion proteins thereof.

a. Production of Immunoconjugates i. Non-Recombinant Methods

In a non-recombinant embodiment of the invention, a targeting molecule, such as an antibody, is linked to a PE molecule of the present invention using any number of means known to those of skill in the art. Both covalent and noncovalent attachment means may be used with PE molecules of the present invention.

The procedure for attaching a PE molecule to an antibody or other targeting molecule ("TM") will vary according to the chemical structure of the TM. Polypeptides typically contain a variety of functional groups; e.g., carboxylic acid (COOH), free amine ($—NH_2$) or sulfhydryl (—SH) groups, which are available for reaction with a suitable functional group on an antibody, for example, to result in the binding of the PE molecule.

Alternatively, the antibody or other TM is derivatized to expose or to attach additional reactive functional groups. The derivatization may involve attachment of any of a number of linker molecules such as those available from Pierce Chemical Company, Rockford Ill.

A "linker", as used herein, is a molecule that is used to join the TM to the PE molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (e.g., through a disulfide linkage to cysteine). However, in a preferred embodiment, the linkers will be joined to the alpha carbon amino and carboxyl groups of the terminal amino acids.

In some circumstances, it is desirable to free the PE molecule from the TM when the immunoconjugate has reached its target site. Therefore, in these circumstances, immunoconjugates will comprise linkages which are cleavable in the vicinity of the target site. Cleavage of the linker to release the PE molecule from the TM may be prompted by enzymatic activity or conditions to which the immunoconjugate is subjected either inside the target cell or in the vicinity of the target site. When the target site is a tumor, a linker which is cleavable under conditions present at the tumor site (e.g. when exposed to tumor-associated enzymes or acidic pH) may be used.

ii. Recombinant Methods

The nucleic acid sequences of the present invention can be prepared by any suitable method including, for example, cloning of appropriate sequences or by direct chemical synthesis by methods such as the phosphotriester method of Narang, et al., *Meth. Enzymol.* 68:90-99 (1979); the phosphodiester method of Brown, et al., *Meth. Enzymol.* 68:109-151 (1979); the diethylphosphoramidite method of Beaucage, et al., *Tetra. Lett.* 22:1859-1862 (1981); the solid phase phosphoramidite triester method described by Beaucage & Caruthers, *Tetra. Letts.* 22(20):1859-1862 (1981), e.g., using an automated synthesizer as described in, for example, Needham-VanDevanter, et al. *Nucl. Acids Res.* 12:6159-6168 (1984); and, the solid support method of U.S. Pat. No. 4,458,066. Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences.

In a preferred embodiment, the nucleic acid sequences of this invention are prepared by cloning techniques. Examples of appropriate cloning and sequencing techniques, and instructions sufficient to direct persons of skill through many cloning exercises are found in Sambrook, et al., Molecular Cloning: A Laboratory Manual (2nd Ed.), Vols. 1-3, Cold Spring Harbor Laboratory (1989)), Berger and Kimmel (eds.), Guide to Molecular Cloning Techniques, Academic Press, Inc., San Diego Calif. (1987)), or Ausubel, et al. (eds.), Current Protocols in Molecular Biology, Greene Publishing and Wiley-Interscience, NY (1987). Product information from manufacturers of biological reagents and experimental equipment also provide useful information. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), Invitrogen, San Diego, Calif., and Applied Biosystems (Foster City, Calif.), as well as many other commercial sources known to one of skill.

Nucleic acids encoding native PE can also be modified to form the immunoconjugates of the present invention. Modification by site-directed mutagenesis is well known in the art. Nucleic acids encoding PE can be amplified by in vitro methods. Amplification methods include the polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

In a preferred embodiment, immunoconjugates are prepared by inserting the cDNA which encodes an antibody or other TM of choice into a vector which comprises the cDNA encoding a desired PE of the invention. The insertion is made so that the targeting agent (for ease of discussion, the discussion herein will assume the targeting agent is an Fv, although other targeting agents could be substituted with equal effect) and the PE are read in frame, that is in one continuous polypeptide which contains a functional Fv region and a functional PE region. In a particularly preferred embodiment, cDNA encoding a PE of the invention is ligated to a scFv so that the toxin is located at the carboxyl terminus of the scFv. In other preferred embodiments, cDNA encoding a PE of the invention is ligated to a scFv so that the toxin is located at the amino terminus of the scFv.

Once the nucleic acids encoding a PE, antibody, or an immunoconjugate of the present invention are isolated and cloned, one may express the desired protein in a recombinantly engineered cell such as bacteria, plant, yeast, insect and mammalian cells. It is expected that those of skill in the art are knowledgeable in the numerous expression systems available for expression of proteins including *E. coli*, other bacterial hosts, yeast, and various higher eucaryotic cells such as the COS, CHO, HeLa and myeloma cell lines. No attempt to describe in detail the various methods known for the expression of proteins in prokaryotes or eukaryotes will be made. In brief, the expression of natural or synthetic nucleic acids encoding the isolated proteins of the invention will typically be achieved by operably linking the DNA or cDNA to a promoter (which is either constitutive or inducible), followed by incorporation into an expression cassette. The cassettes can be suitable for replication and integration in either prokaryotes or eukaryotes. Typical expression cassettes contain transcription and translation terminators, initiation sequences, and promoters useful for regulation of the expression of the DNA encoding the protein. To obtain high level expression of a cloned gene, it is desirable to construct expression cassettes which contain, at the minimum, a strong promoter to direct transcription, a ribosome binding site for translational initiation, and a transcription/translation terminator. For *E. coli* this includes a promoter such as the T7, trp, lac, or lambda promoters, a ribosome binding site and preferably a transcription termination signal. For eukaryotic cells, the control sequences can include a promoter and preferably an enhancer derived from immunoglobulin genes, SV40, cytomegalovirus, and a polyadenylation sequence, and may include splice donor and acceptor sequences. The cassettes of the invention can be transferred into the chosen host cell by well-known methods such as calcium chloride transformation or electroporation for *E. coli* and calcium phosphate treatment, electroporation or lipofection for mammalian cells. Cells transformed by the cassettes can be selected by resistance to antibiotics conferred by genes contained in the cassettes, such as the amp, gpt, neo and hyg genes.

One of skill would recognize that modifications can be made to a nucleic acid encoding a polypeptide of the present invention (i.e., PE or an immunoconjugate formed from a PE of the invention) without diminishing its biological activity. Some modifications may be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids (such as poly His) to aid in purification steps.

In addition to recombinant methods, the immunoconjugates and PEs of the present invention can also be constructed in whole or in part using standard peptide synthesis. Solid phase synthesis of the polypeptides of the present invention of less than about 50 amino acids in length may be accomplished by attaching the C-terminal amino acid of the sequence to an insoluble support followed by sequential addition of the remaining amino acids in the sequence. Techniques for solid phase synthesis are described by Barany & Merrifield, The Peptides: Analysis, Synthesis, Biology. Vol. 2: Special Methods in Peptide Synthesis, Part A. pp. 3-284; Merrifield, et al. *J. Am. Chem. Soc.* 85:2149-2156 (1963), and Stewart, et al., Solid Phase Peptide Synthesis, 2nd ed. , Pierce Chem. Co., Rockford, Ill. (1984). Proteins of greater length may be synthesized by condensation of the amino and carboxyl termini of shorter fragments. Methods of forming peptide bonds by activation of a carboxyl terminal end (e.g., by the use of the coupling reagent N, N'-dicycylohexylcarbodiimide) are known to those of skill.

iii. Purification

Once expressed, the recombinant immunoconjugates and PEs of the present invention can be purified according to standard procedures of the art, including ammonium sulfate precipitation, affinity columns, column chromatography, and the like (see, generally, R. Scopes, Protein Purification, Springer-Verlag, N.Y. (1982)). Substantially pure compositions of at least about 90 to 95% homogeneity are preferred, and 98 to 99% or more homogeneity are most preferred for pharmaceutical uses. Once purified, partially or to homogeneity as desired, if to be used therapeutically, the polypeptides should be substantially free of endotoxin.

Methods for expression of single chain antibodies and/or refolding to an appropriate active form, including single chain antibodies, from bacteria such as *E. coli* have been described and are well-known and are applicable to the antibodies of this invention. See, Buchner, et al., *Anal. Biochem.* 205:263-270 (1992); Pluckthun, *Biotechnology* 9:545 (1991); Huse, et al., *Science* 246:1275 (1989) and Ward, et al., *Nature* 341:544 (1989), all incorporated by reference herein.

Often, functional heterologous proteins from *E. coli* or other bacteria are isolated from inclusion bodies and require solubilization using strong denaturants, and subsequent refolding. During the solubilization step, as is well-known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena, et al., *Biochemistry* 9: 5015-5021 (1970), incorporated by reference herein, and especially as described by Buchner, et al., supra.

Renaturation is typically accomplished by dilution (e.g., 100-fold) of the denatured and reduced protein into refolding buffer. An exemplary buffer is 0.1 M Tris, pH 8.0, 0.5 M L-arginine, 8 mM oxidized glutathione, and 2 mM EDTA.

As a modification to the two chain antibody purification protocol, the heavy and light chain regions are separately solubilized and reduced and then combined in the refolding solution. A preferred yield is obtained when these two proteins are mixed in a molar ratio such that a 5 fold molar excess of one protein over the other is not exceeded. It is desirable to add excess oxidized glutathione or other oxidizing low molecular weight compounds to the refolding solution after the redox-shuffling is completed.

b. Targeting Moiety i. Target Cell Surface Markers

The targeting component of the chimeric molecule can be against a cell surface marker. The cell surface marker can be a protein or a carbohydrate. The cell surface antigen can be a tumor associated antigen. Preferably, the cell surface marker is exclusively expressed, preferentially expressed or expressed at clinically relevant higher levels on cancer cells or other aberrantly proliferating cells. Cell surface antigens that are targets for chimeric molecules are well known in the art, and summarized, e.g., in Mufson, *Front Biosci* (2006) 11:337-43; Frankel, *Clin Cancer Res* (2000) 6:326-334 and Kreitman, *AAPS Journal* (2006) 8(3):E532-E551.

Exemplary cell surface marker targets include cell surface receptors. Cell surface receptor that can be targeted using a toxin of the present invention include, but are not limited to, transferrin receptor, EGF receptor, CD19, CD22, CD25, CD21, CD79, mesothelin and cadherin. Additional cell surface antigens subject to targeted immunotoxin therapy include without limitation MUC1, MAGE, PRAME, CEA, PSA, PSMA, GM-CSFR, CD56, HER2/neu, erbB-2, CD5, CD7. Other cell surface tumor associated antigens are known and find use as targets.

The antigen targets can be found on numerous different types of cancer cells, including without limitation neuroblastoma, intestine carcinoma, rectum carcinoma, colon carcinoma, familiary adenomatous polyposis carcinoma, hereditary non-polyposis colorectal cancer, esophageal carcinoma, labial carcinoma, larynx carcinoma, hypopharynx carcinoma, tong carcinoma, salivary gland carcinoma, gastric carcinoma, adenocarcinoma, medullary thyroid carcinoma, papillary thyroid carcinoma, follicular thyroid carcinoma, anaplastic thyroid carcinoma, renal carcinoma, kidney parenchym carcinoma, ovarian carcinoma, cervix carcinoma, uterine corpus carcinoma, endometrial carcinoma, chorion carcinoma, pancreatic carcinoma, prostate carcinoma, testis carcinoma, breast carcinoma, urinary carcinoma, melanoma, brain tumors, glioblastoma, astrocytoma, meningioma, medulloblastoma, peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, hepatocellular carcinoma, gall bladder carcinoma, bronchial carcinoma, small cell lung carcinoma, non-small cell lung carcinoma, multiple myeloma, basalioma, teratoma, retinoblastoma, choroids melanoma, seminoma, rhabdomyosarcoma, craniopharyngeoma, osteosarcoma, chondrosarcoma, myosarcome, liposarcoma, fibrosarcoma, Ewing sarcoma, and plasmocytoma.

In some embodiments, the cell surface marker is mesothelin. Exemplary cancers whose growth, spread and/or progression can be reduced or inhibited by targeting mesothelin include ovarian cancer, mesothelioma, non-small cell lung cancer, lung adenocarcinoma, fallopian tube cancer, head and neck cancer, cervical cancer and pancreatic cancer.

In some embodiments, the cell surface marker is CD22. Exemplary cancers whose growth, spread and/or progression can be reduced or inhibited by targeting CD22 include hairy cell leukemia, chronic lymphocytic leukemia (CLL), prolymphocytic leukemia (PLL), non-Hodgkin's lymphoma, Small Lymphocytic Lymphoma (SLL) and acute lymphatic leukemia (ALL).

In some embodiments, the cell surface marker is CD25. Exemplary cancers whose growth, spread and/or progression can be reduced or inhibited by targeting CD25 include leukemias and lymphomas, including hairy cell leukemia, and Hodgkin's lymphoma.

In some embodiments, the cell surface marker is a carbohydrate, e.g., Lewis Y antigen. Exemplary cancers whose growth, spread and/or progression can be reduced or inhibited by targeting Lewis Y antigen include bladder cancer, breast cancer, ovarian cancer, colorectal cancer, esophageal cancer, gastric cancer, lung cancer and pancreatic cancer.

In some embodiments, the cell surface marker is CD33. Exemplary cancers whose growth, spread and/or progression can be reduced or inhibited by targeting CD33 include acute myeloid leukemia (AML), chronic myelomonocytic leukemia (CML), and myeloproliferative disorders.

ii. Antibody Targeting Moieties

In a preferred embodiment, the targeting moiety is an antibody, preferably an antibody specifically binding to a surface marker on a cell. Accordingly, in some embodiments, the chimeric molecule is an immunotoxin.

In another preferred embodiment, the targeting moiety is an antibody fragment, preferably an antibody fragment specifically binding to a surface marker on a cell. A preferred antibody fragment is a single chain Fv. Herein the construction and characterization of cytotoxin-based immunotoxins wherein the cytotoxin is fused to a scFv are described. Other preferred antibody fragments to which a toxin or cytotoxic fragment can be fused include Fab, Fab', F(ab')2, Fv fragment, a helix-stabilized antibody, a diabody, a disulfide stabilized antibody, and a single domain antibody (e.g., a camelid antibody).

The fusion of a cytotoxin to an antibody or antibody fragment can be either to the N-terminus or C-terminus of the antibody or antibody fragment. Such fusion typically is accomplished employing recombinant DNA technologies.

Numerous antibodies for use in an immunotoxin are known in the art and find use in the present compositions and methods. Exemplary antibodies against tumor antigens include without limitation antibodies against the transferrin receptor (e.g., HB21 and variants thereof), antibodies against CD22 (e.g., RFB4 and variants thereof), antibodies against CD25 (e.g., anti-Tac and variants thereof), antibodies against mesothelin (e.g., SS1, SSP1, HN1, HN2, MN and variants thereof) and antibodies against Lewis Y antigen (e.g., B3 and variants thereof).

Antibodies for inclusion in an immunotoxin and that find use in the present invention have been described, e.g., in U.S. Pat. No. 5,242,824 (anti-transferrin receptor); U.S. Pat. No. 5,846,535 (anti-CD25); U.S. Pat. No. 5,889,157 (anti-Lewis Y); U.S. Pat. No. 5,981,726 (anti-Lewis Y); U.S. Pat. No. 5,990,296 (anti-Lewis Y); U.S. Pat. No. 7,081,518 (anti-mesothelin); U.S. Pat. No. 7,355,012 (anti-CD22 and anti-CD25); U.S. Pat. No. 7,368,110 (anti-mesothelin); U.S. Pat. No. 7,470,775 (anti-CD30); U.S. Pat. No. 7,521,054 (anti-CD25); U.S. Pat. No. 7,541,034 (anti-CD22); in U.S. Patent Publ. No. 2007/0189962 (anti-CD22), and reviewed in, e.g., Frankel, *Clin Cancer Res* (2000) 6:326-334 and Kreitman, *AAPS Journal* (2006) 8(3):E532-E551.

Numerous immunotoxins successfully used in anticancer and acute graft-versus-host disease are also known in the art, and find use in the present compositions and methods, i.e., by replacing the cytotoxin with an improved PE of the present invention. Exemplary immunotoxins can be found, for example, on the worldwide web at clinicaltrials.gov and include without limitation LMB-2 (Anti-Tac(Fv)-PE38), BL22 and HA22 (RFB4(dsFv)-PE38), SS1P (SS1(dsFv)-PE38), HB21-PE40. Additional immunotoxins of use are described in the patents listed above and herein, and are reviewed in, e.g., Frankel, *Clin Cancer Res* (2000) 6:326-334 and Kreitman, *AAPS Journal* (2006) 8(3):E532-E551.

In some embodiments, the antibody is the Fv portion of HA22. HA22 is a recently developed, improved form of BL22. In HA22, residues SSY in the CDR3 of the antibody variable region heavy chain ("$V_H$") were mutated to THW. Compared to its parental antibody, RFB4, HA22 has a 5-10-fold increase in cytotoxic activity on various CD22-positive cell lines and is up to 50 times more cytotoxic to cells from patients with CLL and HCL (Salvatore, G., et al., *Clin Cancer Res,* 8(4):995-1002 (2002); see also, co-owned application PCT/US02/30316, International Publication WO 03/027135).

SS1P has been shown to specifically kill mesothelin expressing cell lines and to cause regressions of mesothelin expressing tumors in mice (Hassan, R. et al., Clin Cancer Res 8:3520-6 (2002); Onda, M. et al., Cancer Res 61:5070-7 (2001)). Based on these studies and appropriate safety data, 2 phase I trials with SS1P are being conducted at the National Cancer Institute in patients with mesothelin expressing cancers (Chowdhury, P. S. et al., Proc Natl Acad Sci USA 95:669-74 (1998); Hassan, R. et al., Proc Am Soc Clin Oncol 21:29a (2002)). In addition, other therapies targeting mesothelin are in preclinical development (Thomas, A. M. et al., J Exp Med 200:297-306 (2004)). HN1 and HN2 are human anti-mesothelin antibodies, described, e.g., in Feng, et al., *Mol Cancer Ther* (2009) 8(5): I 113-8.

HA22-LR and SS1P-LR are lysosomal resistant variants of the HA22 and SS1P immunotoxins where cleavage clusters for lysosomal proteases have been removed. These variants are described, e.g., in Weldon, et al., *Blood*, (2009) 113(16): 3792-800 and in WO 2009/032954.

iii. Non-Antibody Targeting Moieties

In another preferred embodiment, the targeting moiety is a ligand specifically binding to a receptor on a cell surface. The ligand can be any ligand which binds to a cell surface marker. A preferred ligand is VEGF, Fas, TRAIL, a cytokine (e.g., IL-2, IL-15, IL-4, IL-13), a lymphokine, a hormone, a growth factor (e.g., TGFα, neuronal growth factor, epidermal growth factor).

4. Pharmaceutical Compositions and Administration

In one aspect the present invention provides a pharmaceutical composition or a medicament comprising at least one chimeric protein of the present invention, preferably a targeted toxin, and optionally a pharmaceutically acceptable carrier. A pharmaceutical composition or medicament can be administered to a patient for the treatment of a condition, including, but not limited to, a malignant disease or cancer.

a. Formulation

Pharmaceutical compositions or medicaments for use in the present invention can be formulated by standard techniques using one or more physiologically acceptable carriers or excipients. Suitable pharmaceutical carriers are described herein and in *Remington: The Science and Practice of Pharmacy,* $21^{st}$ Ed., University of the Sciences in Philadelphia, Lippencott Williams & Wilkins (2005). The chimeric proteins of the present invention can be formulated for administration by any suitable route, including via inhalation, topically, nasally, orally, parenterally, or rectally. Thus, the administration of the pharmaceutical composition may be made by intradermal, subdermal, intravenous, intramuscular, intranasal, inhalationally, intracerebral, intratracheal, intraarterial, intraperitoneal, intravesical, intrapleural, intracoronary, subcutaneously or intratumoral injection, with a syringe or other devices. Transdermal administration is also contemplated, as are inhalation or aerosol administration. Tablets and capsules can be administered orally, rectally or vaginally.

The compositions for administration will commonly comprise a solution of the chimeric protein, preferably a targeted toxin, dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of fusion protein in these formulations can vary widely, and will be selected primarily based on fluid volumes, viscosities, body weight and the like in accordance with the particular mode of administration selected and the patient's needs.

The targeted toxin compositions of this invention are suited for parenteral administration, including intravenous administration or administration into a body cavity.

The chimeric proteins, preferably targeted toxins, of the present invention can be formulated for parenteral administration by injection, for example by bolus injection or continuous infusion. Formulations for injection can be presented in unit dosage form, for example, in ampoules or in multidose containers, with an added preservative. Injectable compositions are preferably aqueous isotonic solutions or suspensions, and suppositories are preferably prepared from fatty emulsions or suspensions. The compositions may be sterilized and/or contain adjuvants, such as preserving, stabilizing, wetting or emulsifying agents, solution promoters, salts for regulating the osmotic pressure and/or buffers. Alternatively, the active ingredient can be in powder form for constitution with a suitable vehicle, for example, sterile pyrogen-free water, before use. In addition, they may also contain other therapeutically valuable substances. The compositions are prepared according to conventional mixing, granulating or coating methods, respectively, and contain about 0.1 to 75%, preferably about 1 to 50%, of the active ingredient.

Controlled release parenteral formulations of the targeted toxin compositions of the present invention can be made as implants, oily injections, or as particulate systems. For a broad overview of protein delivery systems see, Banga, A. J., Therapeutic Peptides and Proteins: Formulation, Processing, and Delivery Systems, Technomic Publishing Company, Inc., Lancaster, Pa., (1995) incorporated herein by reference. Particulate systems include microspheres, microparticles, microcapsules, nanocapsules, nanospheres, and nanoparticles. Microcapsules contain the therapeutic protein as a central core. In microspheres the therapeutic is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly. See, e.g., Kreuter J., Colloidal Drug Delivery Systems, J. Kreuter, ed., Marcel Dekker, Inc., New York, N.Y., pp. 219-342 (1994); and Tice & Tabibi, Treatise on Controlled Drug Delivery, A. Kydonieus, ed., Marcel Dekker, Inc. New York, N.Y., pp. 315-339 (1992), both of which are incorporated herein by reference.

Polymers can be used for ion-controlled release of targeted toxin compositions of the present invention. Various degradable and nondegradable polymeric matrices for use in controlled drug delivery are known in the art (Langer R., *Accounts Chem. Res.,* 26:537-542 (1993)). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston et al., *Pharm. Res.,* 9:425-434 (1992); and Pec et al., *J. Parent. Sci. Tech.,* 44(2):58-65 (1990)). Alternatively, hydroxyapatite has been used as a microcarrier for controlled release of proteins (Ijntema et al., *Int. J. Pharm.,* 112:215-224 (1994)). In yet another aspect, liposomes are used for controlled release as well as drug targeting of the lipid-capsulated drug (Betageri et al., Liposome Drug Delivery Systems, Technomic Publishing Co., Inc., Lancaster, Pa. (1993)). Numerous additional systems for controlled delivery of therapeutic proteins are known. See, e.g., U.S. Pat. Nos. 5,055,303, 5,188,837, 4,235,871, 4,501,728, 4,837,028 4,957,735 and 5,019,369, 5,055,303; 5,514,670; 5,413,797; 5,268,164; 5,004,697; 4,902,505; 5,506,206, 5,271,961; 5,254,342 and 5,534,496, each of which is incorporated herein by reference.

Suitable formulations for transdermal application include an effective amount of a composition of the present invention with a carrier. Preferred carriers include absorbable pharmacologically acceptable solvents to assist passage through the skin of the host. For example, transdermal devices are in the form of a bandage comprising a backing member, a reservoir containing the composition optionally with carriers, optionally a rate controlling barrier to deliver the composition to the skin of the host at a controlled and predetermined rate over a prolonged period of time, and means to secure the device to the skin. Matrix transdermal formulations may also be used.

Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

For oral administration, a pharmaceutical composition or a medicament can take the form of, for example, a tablet or a capsule prepared by conventional means with a pharmaceutically acceptable excipient. Preferred are tablets and gelatin capsules comprising the active ingredient, i.e., a composition of the present invention, together with (a) diluents or fillers, e.g., lactose, dextrose, sucrose, mannitol, sorbitol, cellulose (e.g., ethyl cellulose, microcrystalline cellulose), glycine, pectin, polyacrylates and/or calcium hydrogen phosphate, calcium sulfate, (b) lubricants, e.g., silica, talcum, stearic acid, its magnesium or calcium salt, metallic stearates, colloidal silicon dioxide, hydrogenated vegetable oil, corn starch, sodium benzoate, sodium acetate and/or polyethyleneglycol; for tablets also (c) binders, e.g., magnesium aluminum silicate, starch paste, gelatin, tragacanth, methylcellulose, sodium carboxymethylcellulose, polyvinylpyrrolidone and/or hydroxypropyl methylcellulose; if desired (d) disintegrants, e.g., starches (e.g., potato starch or sodium starch), glycolate, agar, alginic acid or its sodium salt, or effervescent mixtures; (e) wetting agents, e.g., sodium lauryl sulphate, and/or (f) absorbents, colorants, flavors and sweeteners.

Tablets may be either film coated or enteric coated according to methods known in the art. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active composition.

For administration by inhalation the chimeric protein, preferably an antibody and/or targeted toxin may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, 1,1,1,2-tetrafluoreethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the chimeric protein, preferably an antibody and/or targeted toxin and a suitable powder base, for example, lactose or starch.

The compositions can also be formulated in rectal compositions, for example, suppositories or retention enemas, for example, containing conventional suppository bases, for example, cocoa butter or other glycerides.

Furthermore, the compositions can be formulated as a depot preparation. Such long-acting formulations can be administered by implantation (for example, subcutaneously or intramuscularly) or by intramuscular injection. Thus, for example, the composition can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device that can contain one or more unit dosage forms containing the active ingredient. The pack can, for example, comprise metal or plastic foil, for example, a blister pack. The pack or dispenser device can be accompanied by instructions for administration.

b. Dosage

In one embodiment of the present invention, a pharmaceutical composition or medicament is administered to a patient at a therapeutically effective dose to prevent, treat, or control a disease or malignant condition, such as cancer. The pharmaceutical composition or medicament is administered to a patient in an amount sufficient to elicit an effective therapeutic or diagnostic response in the patient. An effective therapeutic or diagnostic response is a response that at least partially arrests or slows the symptoms or complications of the disease or malignant condition. An amount adequate to accomplish this is defined as "therapeutically effective dose."

The dosage of chimeric proteins, preferably targeted toxins, or compositions administered is dependent on the species of warm-blooded animal (mammal), the body weight, age, individual condition, surface area of the area to be treated and on the form of administration. The size of the dose also will be determined by the existence, nature, and extent of any adverse effects that accompany the administration of a particular compound in a particular subject. A unit dosage for administration to a mammal of about 50 to 70 kg may contain between about 5 and 500 mg of the active ingredient. Typically, a dosage of the compound of the present invention, is a dosage that is sufficient to achieve the desired effect.

Optimal dosing schedules can be calculated from measurements of chimeric protein, preferably targeted toxin, accumulation in the body of a subject. In general, dosage is from 1 ng to 1,000 mg per kg of body weight and may be given once or more daily, weekly, monthly, or yearly. Persons of ordinary skill in the art can easily determine optimum dosages, dosing methodologies and repetition rates. One of skill in the art will be able to determine optimal dosing for administration of a chimeric protein, preferably a targeted toxin, to a human being following established protocols known in the art and the disclosure herein.

Optimum dosages, toxicity, and therapeutic efficacy of compositions may vary depending on the relative potency of individual compositions and can be determined by standard pharmaceutical procedures in cell cultures or experimental animals, for example, by determining the LD50 (the dose lethal to 50% of the population) and the ED50 (the dose therapeutically effective in 50% of the population). The dose ratio between toxic and therapeutic effects is the therapeutic index and can be expressed as the ratio, $LD_{50}/ED_{50}$. Compositions that exhibit large therapeutic indices are preferred. While compositions that exhibit toxic side effects can be used, care should be taken to design a delivery system that targets such compositions to the site of affected tissue to minimize potential damage to normal cells and, thereby, reduce side effects.

The data obtained from, for example, animal studies (e.g. rodents and monkeys) can be used to formulate a dosage range for use in humans. The dosage of compounds of the present invention lies preferably within a range of circulating concentrations that include the $ED_{50}$ with little or no toxicity. The dosage can vary within this range depending upon the dosage form employed and the route of administration. For any composition for use in the methods of the invention, the therapeutically effective dose can be estimated initially from cell culture assays. A dose can be formulated in animal models to achieve a circulating plasma concentration range that includes the $IC_{50}$ (the concentration of the test compound that achieves a half-maximal inhibition of symptoms) as determined in cell culture. Such information can be used to more accurately determine useful doses in humans. Levels in plasma can be measured, for example, by high performance liquid chromatography (HPLC). In general, the dose equivalent of a chimeric protein, preferably a targeted toxin is from about 1 ng/kg to 100 mg/kg for a typical subject.

A typical targeted toxin composition of the present invention for intravenous administration would be about 0.1 to 10 mg per patient per day. Dosages from 0.1 up to about 100 mg per patient per day may be used. Actual methods for preparing administrable compositions will be known or apparent to those skilled in the art and are described in more detail in such publications as *Remington: The Science and Practice of Pharmacy,* $21^{st}$ Ed., University of the Sciences in Philadelphia, Lippencott Williams & Wilkins (2005).

Exemplary doses of the compositions described herein, include milligram or microgram amounts of the composition per kilogram of subject or sample weight (e.g., about 1 microgram per-kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a composition depend upon the potency of the composition with respect to the desired effect to be achieved. When one or more of these compositions is to be administered to a mammal, a physician, veterinarian, or researcher may, for example, prescribe a relatively low dose at first, subsequently increasing the dose until an appropriate response is obtained. In addition, it is understood that the specific dose level for any particular mammal subject will depend upon a variety of factors including the activity of the specific composition employed, the age, body weight, general health, gender, and diet of the subject, the time of administration, the route of administration, the rate of excretion, any drug combination, and the degree of expression or activity to be modulated.

In one embodiment of the present invention, a pharmaceutical composition or medicament comprising a chimeric protein, preferably a targeted toxin, of the present invention is administered, e.g., in a daily dose in the range from about 1 mg of compound per kg of subject weight (1 mg/kg) to about 1 g/kg. In another embodiment, the dose is a dose in the range of about 5 mg/kg to about 500 mg/kg. In yet another embodiment, the dose is about 10 mg/kg to about 250 mg/kg. In another embodiment, the dose is about 25 mg/kg to about 150 mg/kg. A preferred dose is about 10 mg/kg. The daily dose can be administered once per day or divided into subdoses and administered in multiple doses, e.g., twice, three times, or four times per day. However, as will be appreciated by a skilled artisan, compositions described herein may be administered in different amounts and at different times. The skilled artisan will also appreciate that certain factors may influence the dosage and timing required to effectively treat a subject, including but not limited to the severity of the disease or malignant condition, previous treatments, the general health and/or age of the subject, and other diseases present. Moreover, treatment of a subject with a therapeutically effective amount of a composition can include a single treatment or, preferably, can include a series of treatments.

Exemplary doses of ABT-263 are 100-500 mg daily doses as needed. ABT-263 can be administered at a concentration of about 25 mg/mL to about 50 mg/mL. Exemplary doses of ABT-737 are about 50-200 mg/kg, for example, about 100 mg/kg daily doses.

Following successful treatment, it may be desirable to have the subject undergo maintenance therapy to prevent the recurrence of the disease or malignant condition treated.

c. Administration

The compositions of the present invention can be administered for therapeutic treatments. In therapeutic applications, compositions are administered to a patient suffering from a disease or malignant condition, such as cancer, in an amount sufficient to cure or at least partially arrest the disease and its complications. An amount adequate to accomplish this is defined as a "therapeutically effective dose." Amounts effective for this use will depend upon the severity of the disease and the general state of the patient's health. An effective amount of the compound is that which provides either subjective relief of a symptom(s) or an objectively identifiable improvement as noted by the clinician or other qualified observer.

Determination of an effective amount is well within the capability of those skilled in the art, especially in light of the detailed disclosure provided herein. Generally, an efficacious or effective amount of an immunoconjugate is determined by first administering a low dose or small amount of the immunoconjugate, and then incrementally increasing the administered dose or dosages, adding a second or third medication as needed, until a desired effect of is observed in the treated subject with minimal or no toxic side effects.

Single or multiple administrations of the compositions are administered depending on the dosage and frequency as required and tolerated by the patient. In any event, the composition should provide a sufficient quantity of the proteins of this invention to effectively treat the patient. Preferably, the dosage is administered once but may be applied periodically until either a therapeutic result is achieved or until side effects warrant discontinuation of therapy. Generally, the dose is sufficient to treat or ameliorate symptoms or signs of disease without producing unacceptable toxicity to the patient.

To achieve the desired therapeutic effect, compositions may be administered for multiple days at the therapeutically effective daily dose. Thus, therapeutically effective administration of compositions to treat a disease or malignant condition described herein in a subject may require periodic (e.g., daily) administration that continues for a period ranging from three days to two weeks or longer. Typically, compositions will be administered for at least three consecutive days, often for at least five consecutive days, more often for at least ten, and sometimes for 20, 30, 40 or more consecutive days. While consecutive daily doses are a preferred route to achieve a therapeutically effective dose, a therapeutically beneficial effect can be achieved even if the compounds or compositions are not administered daily, so long as the administration is repeated frequently enough to maintain a therapeutically effective concentration of the composition in the subject. For example, one can administer a composition every other day, every third day, or, if higher dose ranges are employed and tolerated by the subject, once a week.

Among various uses of the targeted toxins of the present invention are included a variety of disease conditions caused by specific human cells that may be eliminated by the toxic action of the fusion protein. For example, the targeted cells might express a cell surface marker such as mesothelin, CD22 or CD25.

5. Methods of Inhibiting Tumor Growth

The compositions of the present invention find use in a variety of ways. For example, the PE molecules of the present invention, e.g., as part of a chimeric molecule, find use to (i) induce apoptosis in a cell bearing one or more surface markers (ii) inhibit unwanted growth, hyperproliferation or survival of a cell bearing one or more cell surface markers, (iii) treat a condition, such as a cancer, and (iv) provide therapy for a mammal having developed a disease caused by the presence of cells bearing one or more cell surface marker.

Any cell or tumor cell expressing one or more cell surface marker, preferably a cell surface receptor, e.g., as described herein, can be used to practice a method of the present invention. A preferred cell or tumor cell expressing a surface marker is s selected from the group consisting of neuroblastoma, intestine carcinoma, rectum carcinoma, colon carcinoma, familiary adenomatous polyposis carcinoma, hereditary non-polyposis colorectal cancer, esophageal carcinoma, labial carcinoma, larynx carcinoma, hypopharynx carcinoma, tong carcinoma, salivary gland carcinoma, gastric carcinoma, adenocarcinoma, medullary thyroid carcinoma, papillary thyroid carcinoma, follicular thyroid carcinoma, anaplastic thyroid carcinoma, renal carcinoma, kidney parenchym carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors, glioblastoma, astrocytoma, meningioma, medulloblastoma, peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, hepatocellular carcinoma, gall bladder carcinoma, bronchial carcinoma, small cell lung carcinoma, non-small cell lung carcinoma, multiple myeloma, basalioma, teratoma, retinoblastoma, choroids melanoma, seminoma, rhabdomyosarcoma, craniopharyngeoma, osteosarcoma, chondrosarcoma, myosarcome, liposarcoma, fibrosarcoma, Ewing sarcoma, and plasmocytoma.

Methods of the present invention can be practiced in vitro or in vivo. When referring to a cell, it is understood that that this term also includes a population of cells, i.e., more than one cell.

Using Compositions for Inducing Apoptosis in a Cell Bearing One or More Cell Surface Markers Apoptosis plays a central role in both the development and homeostasis of multicellular organisms. "Apoptosis" refers to programmed cell death and is characterized by certain cellular characteristics, such as membrane blobbing, chromatin condensation and fragmentation, formation of apoptotic bodies and a [positive "TUNEL" (terminal deoxynucleotidyl transferase-mediated UTP nick end-labeling) staining pattern. A later step in apoptotic process is the degradation of the plasma membrane, rendering apoptotic cells leaky to various dyes (e.g., propidium iodide).

Apoptosis can be induced by multiple independent signaling pathways that converge upon a final effector mechanism consisting of multiple interactions between several death receptors and their ligands, which belong to the tumor necrosis factor (TNF) receptor/ligand superfamily. The best-characterized death receptors are CD95 ("Fas"), TNFR1 (p55), death receptor 3 (DR3 or Apo3/TRAMO), DR4 and DR5 (apo2-TRAIL-R2). The final effector mechanism of apoptosis is the activation of a series of proteinases designated as caspases. The activation of these caspases results in the cleavage of a series of vital cellular proteins and cell death.

The present invention provides methods for inducing apoptosis in a cell expressing one or more cell surface marker. In one aspect, the method for inducing apoptosis in a cell comprises the step of exposing or contacting the cell expressing one or more cell surface marker, such as a cell surface receptor, to a PE of the present invention, e.g., as part of chimeric molecule, as described herein. Typically, the cells are exposed to or contacted with effective amounts of the immunoconjugate, wherein the contacting results in inducing apoptosis.

In another aspect of present invention, a method of inducing a tumor cell expressing one or more cell surface marker to undergo apoptosis is provided comprising the step of administering to a subject a PE of the present invention, e.g., as part of a chimeric molecule.

Using Compositions for Inhibiting Growth, Hyperproliferation, or Survival of A Cell Bearing One or More Cell Surface Marker It is an object of the present invention to provide improved therapeutic strategies for treatment of cancers using the compositions of the invention. In one aspect of the present invention, a method for inhibiting at least one of unwanted growth, hyperproliferation, or survival of a cell is provided. This method comprises the step of contacting a cell expressing a surface marker with an effective amount of a PE of the present invention, e.g., as part of a chimeric molecule, as described herein, wherein the step of contacting results in the inhibition of at least one of unwanted growth, hyperproliferation, or survival of the cell. In one embodiment, this method comprises the step of determining whether the cell expresses one or more cell surface markers, for example, a cell surface receptor. Typically, the cells are exposed to or contacted with an effective amounts of the immunoconjugate, wherein the contacting results in the inhibition of at least one of unwanted growth, hyperproliferation, or survival of the cell.

Thus, in one aspect of the present invention methods of inhibiting growth of a population of cells bearing one or more cell surface markers are provided. In a preferred embodiment, this method comprises the steps of (a) contacting a population of cells with a chimeric protein comprising (i) a targeting moiety which specifically binds at least one of the cell surface markers and (ii) a PE of the present invention, e.g., with Gly, Ala or Ser substitutions at D406 and Q592. Thereby the growth of the population of cells is inhibited.

Many tumors form metastasis. Thus, in another aspect of the present invention, the compositions of the present invention are used to prevent the formation of a metastasis. This method comprises the step of administering to a tumor cell a composition of the present invention wherein the administering results in the prevention of metastasis. In a preferred embodiment, the composition comprises a targeted toxin comprising an antibody against a cell surface antigen and a PE of the present invention. Typically, the cells are exposed to or contacted with effective amounts of the immunoconjugate, wherein the contacting results in the prevention of metastasis.

Using Compositions for Treating Cancer

Methods of the present invention can be practiced in vitro and in vivo. Thus, in another aspect of the present invention, a method for treating a subject suffering from a cancerous condition is provided. This method comprises the step of administering to a subject having been diagnosed with a cancer a therapeutically effective amounts of the improved PE molecule, as described herein, wherein the cancerous condition is characterized by unwanted growth or proliferation of a cell expressing one or more cell surface marker, and wherein the step of administering results in the treatment of the subject.

In a preferred embodiment, the composition comprises an immunotoxin with an improved PE of the present invention, or variants thereof. Typically, the cells are exposed to or contacted with effective amounts of the immunotoxin, wherein the contacting results in the treatment of the subject.

Compositions of the present invention can be used to treat any cancer described herein, e.g., those subject to treatment with an immunotoxin. In one embodiment of the present invention, an immunotoxin comprising a PE of the present invention is used to treat a subject suffering from a lung cancer expressing one or more cell surface marker. A lung cancer includes, but is not limited to, bronchogenic carcinoma [squamous cell, undifferentiated small cell, undifferentiated large cell, adenocarcinoma], alveolar [bronchiolar] carcinoma, bronchial adenoma, sarcoma, lymphoma, chondromatous hamartoma, mesothelioma, SCLC, and NSCLC.

In another embodiment of the present invention, a composition of the present invention is used to treat a subject suffering from a sarcoma expressing one or more cell surface marker. A sarcoma includes, but is not limited to, cancers such as angiosarcoma, fibrosarcoma, rhabdomyosarcoma, liposarcoma, myxoma, rhabdomyoma, fibroma, lipoma and teratoma.

In yet another embodiment of the present invention, an immunotoxin comprising a PE of the present invention is used to treat a subject suffering from a gastrointestinal cancer expressing one or more cell surface marker. A gastrointestinal cancer includes, but is not limited to cancers of esophagus [squamous cell carcinoma, adenocarcinoma, leiomyosarcoma, lymphoma], stomach [carcinoma, lymphoma, leiomyosarcoma], pancreas [ductal adenocarcinoma, insulinoma, glucagonoma, gastrinoma, carcinoid tumors, VIPoma], small bowel [adenocarcinoma, lymphoma, carcinoid tumors, Kaposi's sarcoma, leiomyoma, hemangioma, lipoma, neurofibroma, fibroma], and large bowel [adenocarcinoma, tubular adenoma, villous adenoma, hamartoma, leiomyoma].

In one embodiment of the present invention, an immunotoxin comprising a PE of the present invention is used to treat a subject suffering from a cancer of the genitourinary tract expressing one or more cell surface marker. Cancers of the genitourinary tract include, but are not limited to cancers of kidney [adenocarcinoma, Wilms tumor (nephroblastoma), lymphoma, leukemia, renal cell carcinoma], bladder and urethra [squamous cell carcinoma, transitional cell carcinoma, adenocarcinoma], prostate [adenocarcinoma, sarcoma], and testis [seminoma, teratoma, embryonal carcinoma, teratocarcinoma, choriocarcinoma, sarcoma, Leydig cell tumor, fibroma, fibroadenoma, adenomatoid tumors, lipoma].

In another embodiment of the present invention, an immunotoxin comprising a PE of the present invention is used to treat a subject suffering from a liver cancer expressing one or more cell surface marker. A liver cancer includes, but is not limited to, hepatocellular carcinoma, cholangiocarcinoma, hepatoblastoma, angiosarcoma, hepatocellular adenoma, and hemangioma.

In one embodiment of the present invention, an immunotoxin comprising a PE of the present invention is used to treat a subject suffering from a skin cancer expressing one or more cell surface marker. Skin cancer includes, but is not limited to, malignant melanoma, basal cell carcinoma, squamous cell carcinoma, Kaposi's sarcoma, nevi, dysplastic nevi, lipoma, angioma, dermatofibroma, keloids, and psoriasis.

In one embodiment of the present invention, an immunotoxin comprising a PE of the present invention is used to treat a subject suffering from a gynecological cancer expressing one or more cell surface marker. Gynecological cancers include, but are not limited to, cancer of uterus [endometrial carcinoma], cervix [cervical carcinoma, pre-invasive cervical dysplasia], ovaries [ovarian carcinoma (serous cystadenocarcinoma, mucinous cystadenocarcinoma, endometrioid carcinoma, clear cell adenocarcinoma, unclassified carcinoma), granulosa-theca cell tumors, Sertoli-Leydig cell tumors, dysgerminoma, malignant teratoma and other germ cell tumors], vulva [squamous cell carcinoma, intraepithelial carcinoma, adenocarcinoma, fibrosarcoma, melanoma], vagina [clear cell carcinoma, squamous cell carcinoma, sarcoma botryoides (embryonal rhabdomyosarcoma), and fallopian tubes [carcinoma].

In yet another embodiment of the present invention, an immunotoxin comprising a PE of the present invention is used to treat a subject suffering from a bone cancer expressing one or more cell surface marker. Bone cancer includes, but is not limited to, osteogenic sarcoma [osteosarcoma], fibrosarcoma, malignant fibrous histiocytoma, chondrosarcoma, Ewing's sarcoma, malignant lymphoma [reticulum cell sarcoma], multiple myeloma, malignant giant cell tumor, chordoma, osteochondroma [osteocartilaginous exostoses], benign chondroma, chondroblastoma, chondromyxoid fibroma, osteoid osteoma, and giant cell tumors.

In one embodiment of the present invention, an immunotoxin comprising a PE of the present invention is used to treat a subject suffering from a cancer of the nervous system expressing one or more cell surface marker. Cancers of the nervous system include, but are not limited to cancers of skull [osteoma, hemangioma, granuloma, xanthoma, Paget's disease of bone], meninges [meningioma, meningiosarcoma, gliomatosis], brain [astrocytoma, medulloblastoma, glioma, ependymoma, germinoma (pinealoma), glioblastoma multiforme, oligodendroglioma, schwannoma, retinoblastoma, congenital tumors], and spinal cord [neurofibroma, meningioma, glioma, sarcoma].

In one embodiment of the present invention, an immunotoxin comprising a PE of the present invention is used to treat a subject suffering from a hematologic cancer expressing one or more cell surface marker. Hematologic cancers include, but are not limited to cancer of blood [myeloid leukemia (acute and chronic), hairy cell leukemia, acute lymphoblastic leukemia, chronic lymphocytic leukemia, myeloproliferative diseases, multiple myeloma, myelodysplastic syndrome], Hodgkin's disease, and non-Hodgkin's lymphoma (malignant lymphoma).

In one embodiment of the present invention, an immunotoxin comprising a PE of the present invention is used to treat a subject suffering from a cancer mediated by mesothelin-CA125 binding interaction. Exemplary cancers whose growth, spread and/or progression are at least partially mediated by CA125/mesothelin binding include ovarian cancer, mesothelioma, non-small cell lung cancer, lung adenocarcinoma and pancreatic cancer.

In one embodiment of the present invention, an immunotoxin comprising a PE of the present invention is used to treat a subject suffering from a cancer of adrenal glands expressing one or more cell surface marker. A cancer of adrenal glands includes, but is not limited to, neuroblastoma.

Methods for treating cancer may optionally comprise one or more of the following steps: obtaining a biological sample of tissue or fluid from an individual; screening the biological sample for the expression of one or more cell surface marker, preferably a cell surface receptor, for example by contacting the biological sample with an antibody directed to the surface marker, preferably a cell surface receptor; or screening the biological sample for expression of a surface marker polynucleotide, preferably a cell surface receptor polynucleotide, for example by detecting a surface marker mRNA, preferably, a cell surface receptor mRNA. This can be done using standard technologies known in the art, e.g., Western blotting, Northern blotting or PCR.

Using Compositions for Treating A Subject Having Developed A Disease Caused by the Presence of Cells Bearing One or More Cell Surface Markers Also provided is a method a method of providing therapy for a mammal having developed a disease caused by the presence or aberrant proliferation of cells preferentially bearing or overexpressing one or more cell surface markers. In a preferred embodiment, this method comprises the step of administering to said mammal a chimeric protein comprising (i) a targeting moiety which specifically binds to at least one surface marker on said cells and (ii) a PE of the present invention, e.g., with Gly, Ala or Ser substitutions at D406 and Q592A.

In a preferred embodiment, the chimeric protein comprises an immunotoxin with a PE of the present invention, or variants thereof. Typically, the cells are exposed to or contacted with effective amounts of the immunotoxin, wherein the contacting results in the treatment of the subject.

In another embodiment, this invention provides for eliminating target cells in vitro or ex vivo using the PE molecules of the present invention. For example, chimeric molecules comprising the PE molecules of the invention can be used to purge targeted cells from a population of cells in a culture. Thus, for example, cells cultured from a patient having a cancer expressing a targeted cell surface marker (e.g., CD22, CD25, mesothelin, Lewis Y) can be purged of cancer cells by contacting the culture with chimeric molecules directed against the cell surface marker of interest, as described herein.

In some instances, the target cells may be contained within a biological sample. A "biological sample" as used herein is a sample of biological tissue or fluid that contains target cells and non-target cells. Such samples include, but are not limited to, tissue from biopsy, blood, and blood cells (e.g., white cells). A biological sample is typically obtained from a multicellular eukaryote, preferably a mammal such as rat, mouse, cow, dog, guinea pig, or rabbit, and more preferably a primate, such as a macaque, chimpanzee, or human. Most preferably, the sample is from a human.

6. Methods of Monitoring Disease

The invention provides methods of detecting inhibition of tumor growth in a patient suffering from or susceptible to a cancer that can be treated with a targeted toxin, e.g., a cancer with a cell surface marker. The methods are particularly useful for monitoring a course of treatment being administered to a patient using the PE molecules of the present invention, e.g., as part of a chimeric molecule, as described herein. The methods can be used to monitor both therapeutic treatment on symptomatic patients and prophylactic treatment on asymptomatic patients.

The monitoring methods entail determining a baseline value of tumor burden in a patient before administering a dosage of the PE molecules of the present invention, e.g., as part of a chimeric molecule, and comparing this with a value for the tumor burden after treatment, or with the tumor burden in a patient receiving no treatment.

A significant decrease (i.e., greater than the typical margin of experimental error in repeat measurements of the same sample, expressed as one standard deviation from the mean of such measurements) in value of the tumor burden signals a positive treatment outcome (i.e., that administration of the PE molecules of the present invention, e.g., as part of a chimeric molecule, has blocked progression of tumor growth and/or metastasis).

In other methods, a control value (i.e., a mean and standard deviation) of tumor burden is determined for a control population or a normal population (e.g., burden=zero). Typically, the individuals in the control population have not received prior treatment. Measured values of the tumor burden in a patient after administering the PE molecules of the present invention, e.g., as part of a chimeric molecule, are then compared with the control value. A significant decrease in tumor burden relative to the control value (e.g., greater than one standard deviation from the mean) signals a positive treatment outcome. A lack of significant decrease or an increase signals a negative treatment outcome.

In other methods, a control value of tumor burden (e.g., a mean and standard deviation) is determined from a control population of individuals who have undergone treatment receiving a regimen of PE molecules of the present invention, e.g., as part of a chimeric molecule, as described herein. Measured values of tumor burden in a patient are compared with the control value. If the measured level in a patient is not significantly different (e.g., more than one standard deviation) from the control value, treatment can be discontinued. If the tumor burden level in a patient is significantly above the control value, continued administration of agent is warranted.

In other methods, a patient who is not presently receiving treatment but has undergone a previous course of treatment is monitored for tumor burden to determine whether a resumption of treatment is required. The measured value of tumor burden in the patient can be compared with a value of tumor burden previously achieved in the patient after a previous course of treatment. A significant increase in tumor burden relative to the previous measurement (i.e., greater than a typical margin of error in repeat measurements of the same sample) is an indication that treatment can be resumed. Alternatively, the value measured in a patient can be compared with a control value (mean plus standard deviation) determined in a population of patients after undergoing a course of treatment. Alternatively, the measured value in a patient can be compared with a control value in populations of prophylactically treated patients who remain free of symptoms of disease, or populations of therapeutically treated patients who show amelioration of disease characteristics. In all of these cases, a increase in tumor burden relative to the control level (i.e., more than a standard deviation) is an indicator that treatment should be resumed in a patient.

The tissue sample for analysis is typically blood, plasma, serum, mucous, tissue biopsy, tumor, ascites or cerebrospinal fluid from the patient. The sample can analyzed for indication of neoplasia. Neoplasia or tumor burden can be detected using any method known in the art, e.g., visual observation of a biopsy by a qualified pathologist, or other visualization techniques, e.g., radiography, ultrasound, magnetic resonance imaging (MRI).

7. Kits, Containers, Devices, and Systems

For use in diagnostic, research, and therapeutic applications described above, kits and systems are also provided by the invention. Kits of the present invention will comprise a chimeric molecule comprising a PE of the present invention, e.g., as part of a chimeric molecule. The embodiments of the present PE and chimeric molecules are as described herein.

In addition, the kits and systems may include instructional materials containing directions (i.e., protocols) for the practice of the methods of this invention. The instructions may be present in the subject kits in a variety of forms, one or more of which may be present in the kit. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

A wide variety of kits, systems, and compositions can be prepared according to the present invention, depending upon the intended user of the kit and system and the particular needs of the user.

Kits with unit doses of the active composition, e.g. in oral, vaginal, rectal, transdermal, or injectable doses (e.g., for intramuscular, intravenous, or subcutaneous injection), are provided. In such kits, in addition to the containers containing the unit doses will be an informational package insert describing the use and attendant benefits of the composition in treating a disease or malignant condition. Suitable active compositions and unit doses are those described herein above.

Although the forgoing invention has been described in some detail by way of illustration and example for clarity and understanding, it will be readily apparent to one of ordinary skill in the art in light of the teachings of this invention that certain variations, changes, modifications and substitutions of equivalents may be made thereto without necessarily departing from the spirit and scope of this invention. As a result, the embodiments described herein are subject to various modifications, changes and the like, with the scope of this invention being determined solely by reference to the claims appended hereto. Those of skill in the art will readily recognize a variety of non-critical parameters that could be changed, altered or modified to yield essentially similar results. It is also to be understood that the terminology used herein is for the purpose of describing particular embodiments only, and is not intended to be limiting, since the scope of the present invention will be limited only by the appended claims.

While each of the elements of the present invention is described herein as containing multiple embodiments, it should be understood that, unless indicated otherwise, each of the embodiments of a given element of the present invention is capable of being used with each of the embodiments of the other elements of the present invention and each such use is intended to form a distinct embodiment of the present invention.

The referenced patents, patent applications, and scientific literature, including accession numbers to GenBank database sequences, referred to herein are hereby incorporated by reference in their entirety as if each individual publication, patent or patent application were specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

As can be appreciated from the disclosure above, the present invention has a wide variety of applications.

The invention is further illustrated by the following examples, which are only illustrative and are not intended to limit the definition and scope of the invention in any way.

EXAMPLES

The following examples are offered to illustrate, but not to limit the claimed invention.

Example 1

Epitopes Removed in the Present PE molecules: PE-LR-8M

TABLE 1

| Epitope Removed | Mutations |
|---|---|
| 1 | LR (Δ251-273/Δ285-394) |
| 2 | LR, R467A |
| 3 | LR |
| 4 | R432G, D406A |
| 5 | R490A |
| 6 | E548A, R513A |
| 7 | K590S, Q592A |

*Epitopes are described, e.g., in Onda, et al., *Proc Natl Acad Sci USA*. 2008 105(32): 11311-6 and in WO 2007/016150.

Example 2

Cytotoxic Activity of HA22-LR-8M on Cells

HA22-LR-8M has cytotoxicity against Raji and CA46 cells that is comparable to HA22 and HA22-LR-6X. Cells were incubated with various immunotoxins (e.g., HA22, HA22-LR, HA22-LR-6X, HA22-LR-8M) for 2 or 3 days and cell viability was assessed by a WST assay (i.e., cell proliferation was measured using the tetrazolium salt WST-1 (reagents and kits are available from Roche Applied Sciences)). The results are summarized in Table 2.

TABLE 2

| Immunotoxin | $IC_{50}$ (ng/ml) | Cell Line |
|---|---|---|
| HA22 | 0.3 | RAJI |
| LR-8M | 0.5 | RAJI |
| HA22 | 0.13 | RAJI |
| HA22-LR | 0.4 | RAJI |
| HA22-LR-6X | 0.3 | RAJI |
| HA22-LR-8M | 0.2 | RAJI |
| HA22 | 0.33 | CA46 |
| HA22-LR | 0.3 | CA46 |
| HA22-LR-6X | 0.4 | CA46 |
| HA22-LR-8M | 0.33 | CA46 |

HA22—un-mutated form of PE38

HA22 LR—(Δ251-273/Δ285-394)

HA22 LR 6X—(Δ251-273/Δ285-394/R432G, R467A, R490A, R513A, E548S, K590S)

HA22 LR 8X—(Δ251-273/Δ285-394/D406A, R432G, R467A, R490A, R513A, E548S, K590S, Q592A)

The cell killing activity of HA22-LR-8M was tested against chronic lymphatic leukemia (CLL) cells from CLL patients. Cells from patients with CLL were incubated with HA22 (which has an un-mutated form of PE38), HA22-LR or HA22-LR-8M and the concentration that reduced cell viability by 50% ($IC_{50}$) was determined. The $IC_{50}$ for HA22-LR-8M is comparable to HA22-LR, and greatly improved over HA22. The results are shown in FIG. 1.

Example 3

Antitumor Activity and Decreased Immunogenicity of HA22-LR-8M

Figure 2:
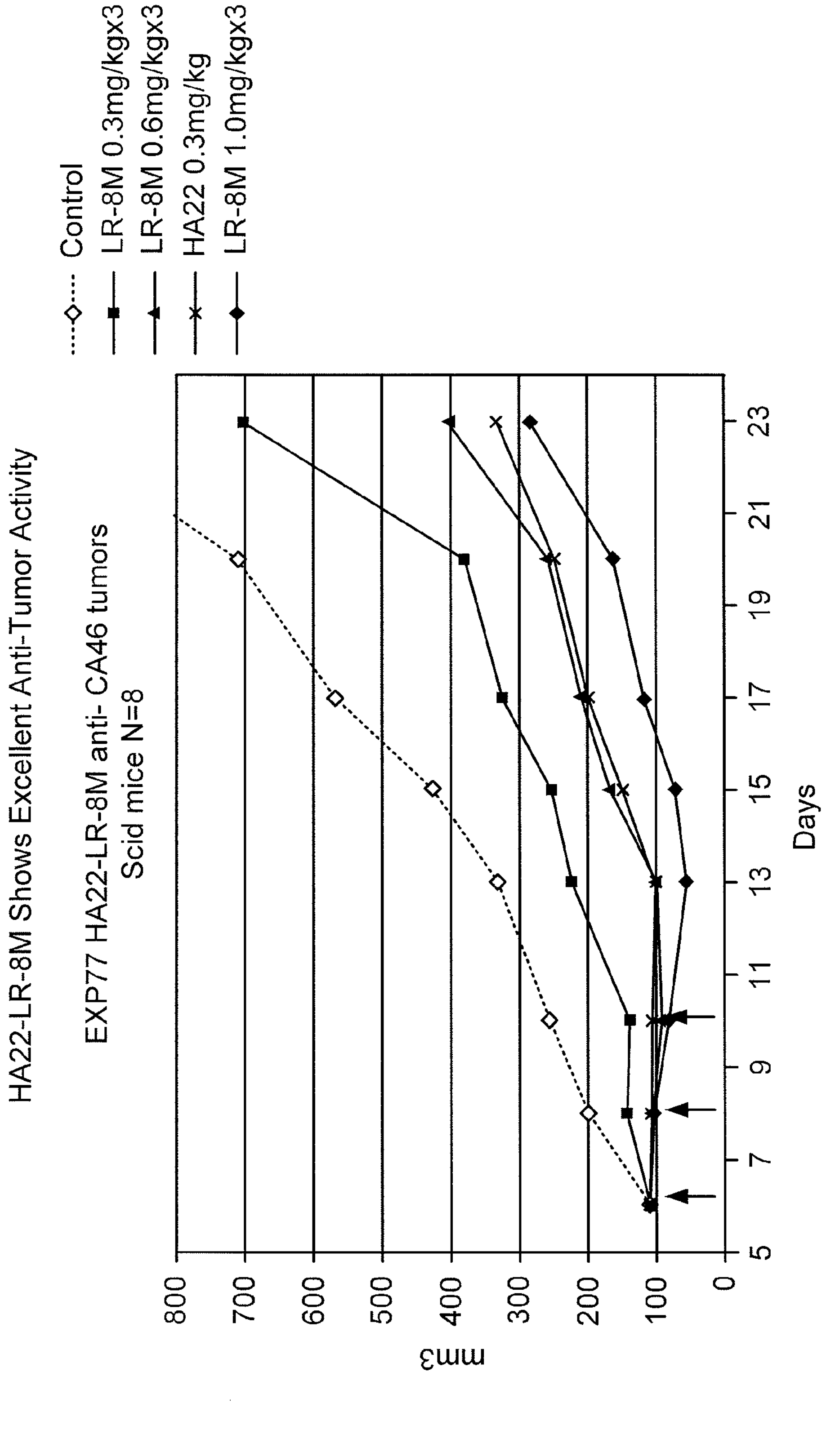
FIG. 2 illustrates that HA22-LR-8M has excellent antitumor activity against CA46 tumors in SCID mice. Mice with CA46 tumors were treated intravenously (i.v.) with 3 injections of HA22 or HA22-LR-8M and the size of the tumors measured for 23 days.

The antitumor activity of HA22-LR-8M was tested against CA46 tumors in SCID mice. Mice with CA46 tumors were treated intravenously (i.v.) with 3 injections of HA22 or HA22-LR-8M and the size of the tumors measured for 23 days. The results are shown in FIG. 2.

Figure 3:
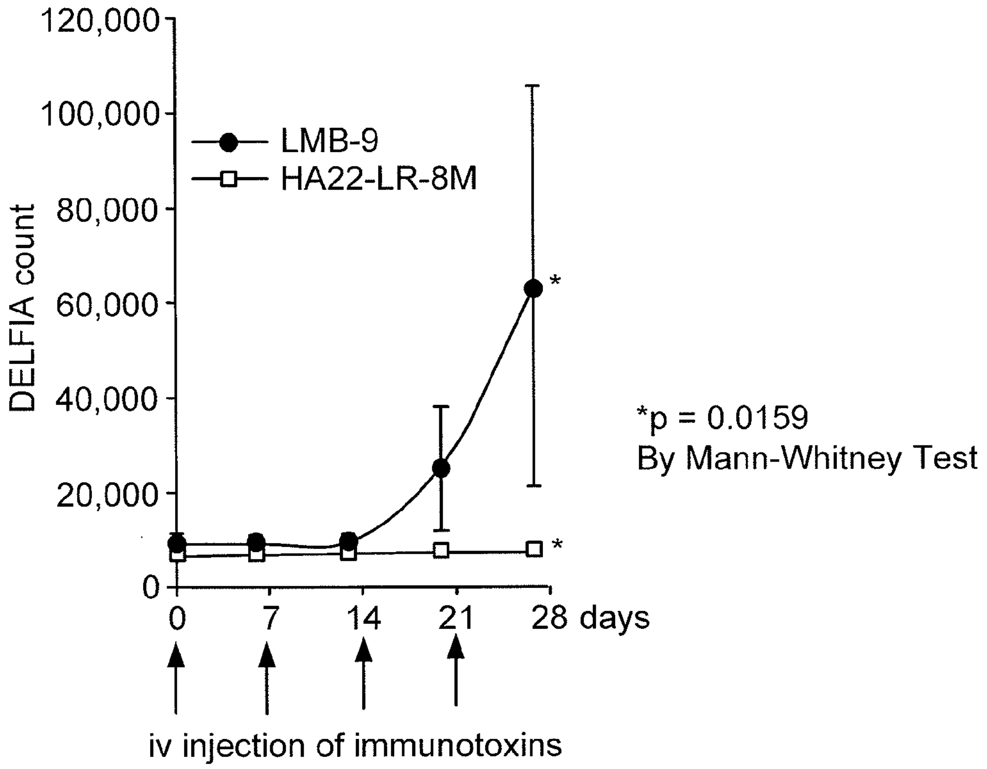
FIG. 3 illustrates the decreased immunogenicity of HA22-LR-8M in comparison to LMB-9 in mice receiving intravenous administrations of the immunotoxins.

The immunogenicity of HA22-LR-8M in comparison to LMB-9 was tested in mice receiving intravenous administrations of the immunotoxins according standard techniques. Mice were injected with immunotoxin LMB9 that has an un-mutated form of PE38 or HA22-LR-8M 4 times at 7 day intervals intravenously. Six (6) days after each injection blood was obtained from the animals and its reactivity with LMB9 or HA22-LR-8M measured by ELISA. Blood samples were collected and stored at minus 80 degrees until the assay. No immunogenic response was elicited even after 4 intravenous administrations of HA22-LR-8M measured over 28 days (FIG. 3).

Figure 4:
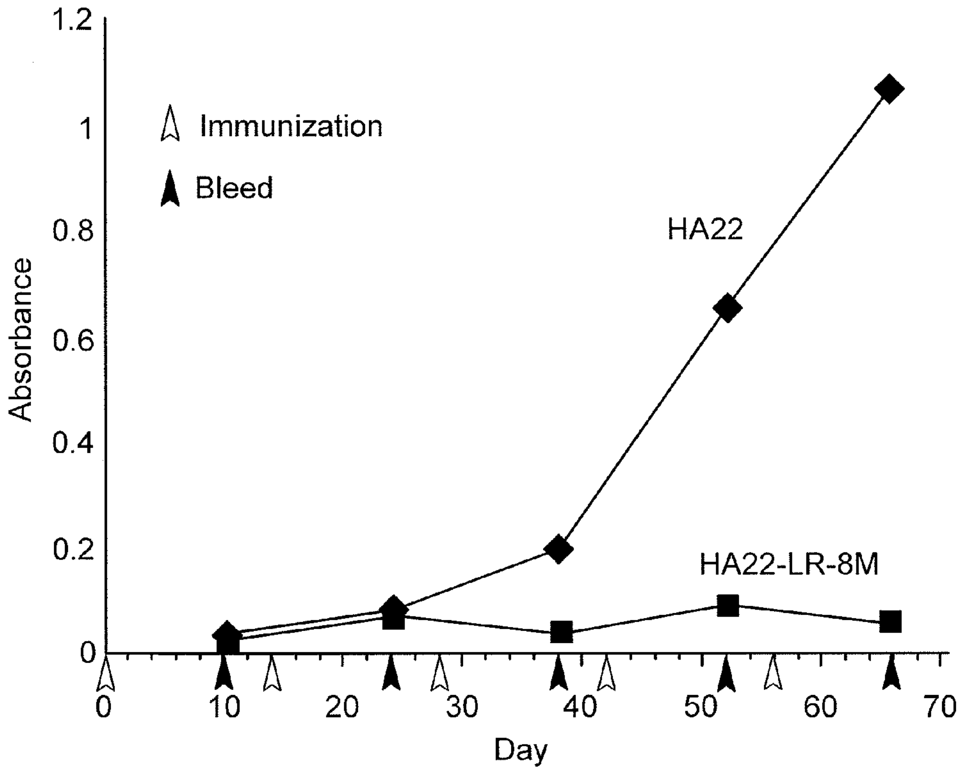
FIG. 4 illustrates the decreased immunogenicity of HA22-LR-8M in comparison to HA22 in mice receiving intravenous (i.v.) administrations of the immunotoxins.

The immunogenicity of HA22-LR-8M in comparison to HA22 was tested in mice receiving intravenous (i.v.) administrations of the immunotoxins according to standard techniques. Mice were injected i.v. every 2 weeks with 5 μg of immunotoxin and bled 10 days later. The serum was analyzed for antibodies reacting with the injected immunotoxin by ELISA. No immunogenic response was elicited even after 5 intravenous administrations of HA22-LR-8M measured over 66 days (FIG. 4).

Example 4

Further Studies of the Biological Activities of HA22-LR-8M

The specific cytotoxic activity of HA22 and HA22-LR-8M on CA46 cells was tested as described above. The results are presented in FIG. 5A, HA22 (closed circle) and HA22-LR-8M (closed square).

Figure 5:
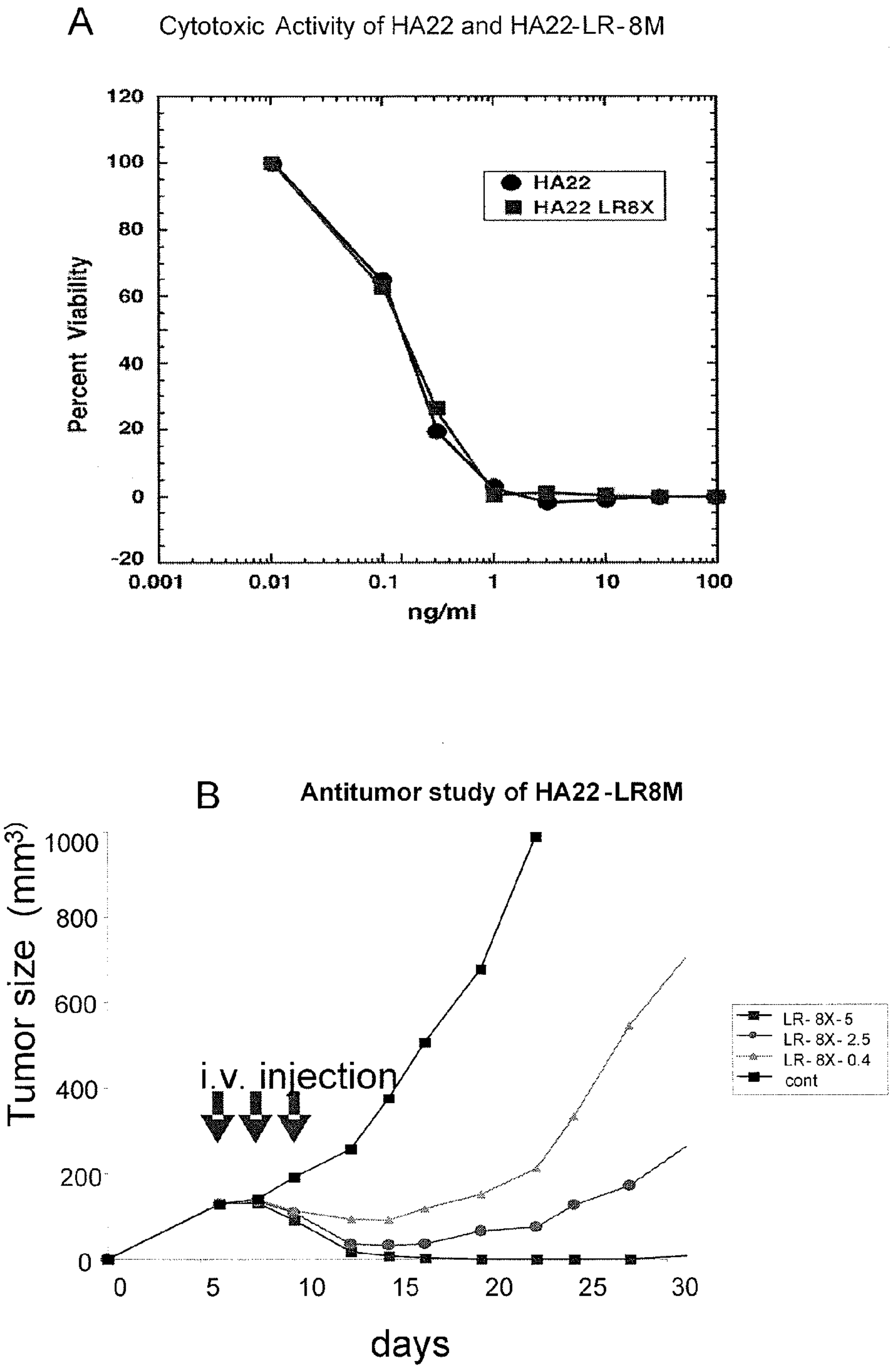
FIG. 5 shows specific cytotoxic activity of HA22 (closed circle) and HA22-LR-8M (closed square) on CA46 cells (FIG. 5A); anti-tumor activity of HA22 and HA22-LR-8M (FIG. 5B).

Anti-tumor activity of HA22 and HA22-LR-8M on SCID mice (FIG. 5B). Groups of eight SCID mice bearing CA46 tumors were treated every other day times three, as indicated by arrows, with PBS/0.2% MSA (black square), or with tree doses of HA22-LR-8M at 0.4 mg/kg (triangle), 2.5 mg/kg (circle), or 5.0 mg/kg (gray square). Tumor size was measured every other day and was calculated using the formula (0.4×a b^2). Data are expressed as the mean +SD. There were significant differences of the anti-tumor activation on day 24 and 27 ($p<0.05$).

Figure 6:
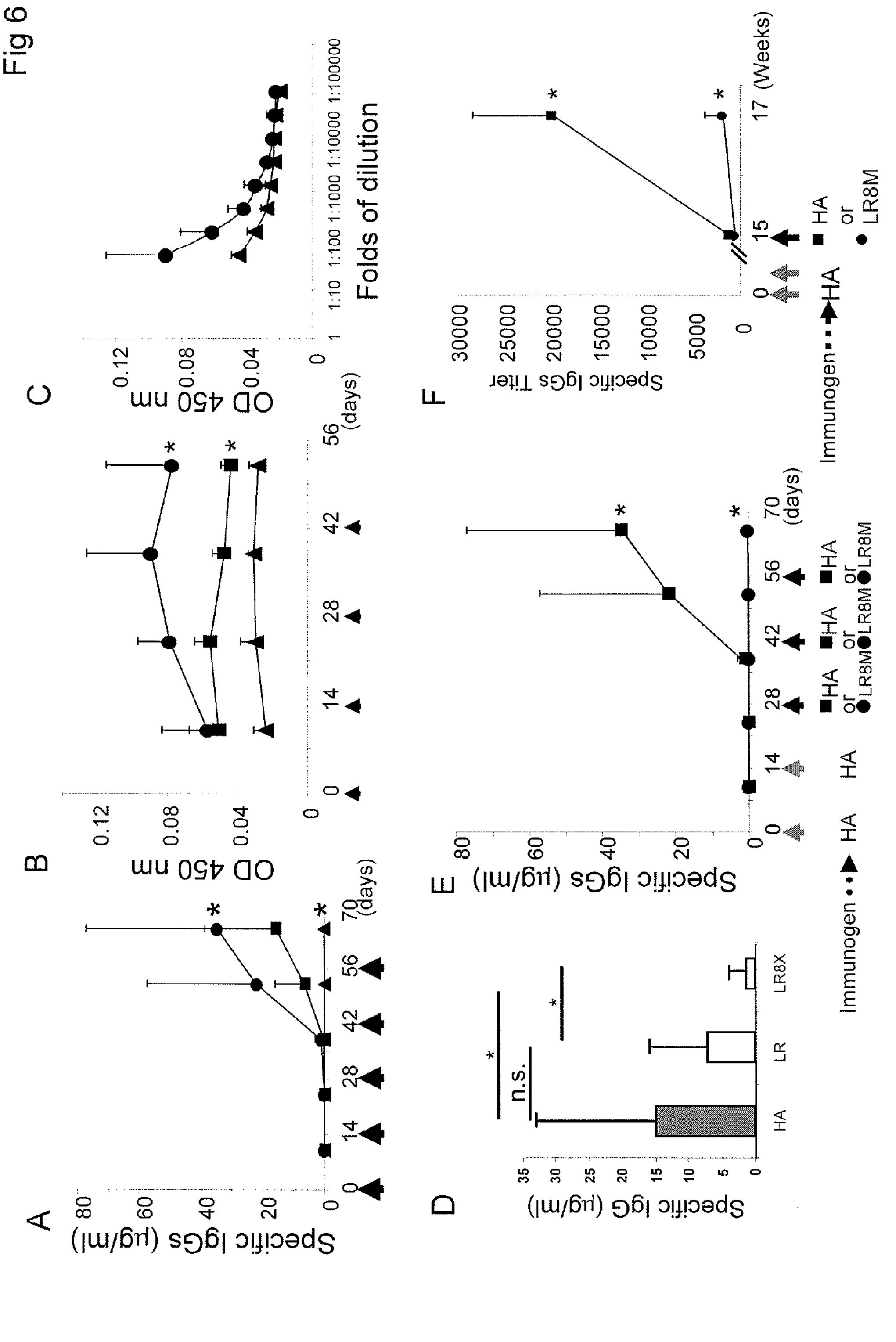
FIG. 6 shows a comparison of the immunological responses to HA22, HA22-8X , and HA22-LR-8M. Generation of the IgG antibodies to the immunotoxins in mice is illustrated in FIG. 6A. IgM responses induced by the immunotoxins in mice are shown in FIG. 6B. Titration of immunized serum is shown in FIG. 6C. The amount of antibodies against each mutant molecule in HA22 immunized mice sera is shown in FIG. 6D. Secondary immune response to HA22 or HA22-LR-8M immunotoxins are shown in FIG. 6E. Immune response of preexisting Ab producing B cells to HA22 or HA22-LR-8M immunotoxins is shown in FIG. 6F.

The immunological responses to HA22, HA22-8X , and HA22-LR-8M were compared. Generation of the IgG antibodies to the immunotoxins in mice is illustrated in FIG. 6A. Groups of Balb/c mice (n=9) received HA22 (250 ug/kg, circle),HA22-8X (250 ug/kg, square), or HA22-LR-8M (500 ug/kg, triangle) i.v. every 14 days (arrows) and were bled 10 days after each injection. Antibody levels were measured on respective immunotoxins using ICC-ELISA according to standard techniques.

IgM responses induced by the immunotoxins in mice was also tested (FIG. 6B). Balb/c mice (10 per group) were intravenously injected every 14 days with HA22 (250 ug/kg, circles), HA22-LR-8M (500 ug/kg, squares) in PBS/0.2% MSA, or PBS/0.2%MSA alone (triangles) as control. The mice were bled 10 days after each injection and the 50 fold diluted sera assayed for IgM against respective immunotoxins with ICC-ELISA. Titration of immunized serum is shown in FIG. 6C. The day 38 sera from mice immunized with HA22 (circles) were also serially diluted and compared with the control sera immunized with PBS/0.2% MSA (triangles) alone for IgM against HA22. IgM levels were measured using ICC-ELISA with each immunotoxin.

Amount of antibodies against each mutant molecule in HA22 immunized mice sera was tested (FIG. 6D). 10 Balb/c mice received HA22 (250 ug/kg) i.v. every 14 days (total 4 injectons) and were bled 10 days after the 4th injection. Antibody levels against HA22 were measured using ICC-ELISA with HA22. Cross-reactivity of the HA treated sera against mutant immunotoxins were also measued using ICC-ELISA with the respective immunotoxins.

Secondary immune response to HA22 or HA22-LR-8M immunotoxins were studied (FIG. 6E). 4 weeks after primary immunization with HA22 (5 ug, 2 times immunization with 2 weeks interval), mice were re-immunized with HA22 (squares) or HA22-LR-8M (circles). Specific IgGs levels for each immunotoxin are shown.

Immune response of preexisting Ab producing B cells to HA22 or HA22-LR-8M immunotoxins (FIG. 6F). On 15 weeks after 3 or 4 i.v. immunizations with HA22 (5 ug/mouse), 8 mice which have low titer (about 103) of anti-HA22 specific IgG, were selected for further re-immunization study. Mice were re-immunized with HA22 (squares) or HA22-LR-8M (circles). Each immunotoxin specific IgG titer is shown. The amount of Abs were expressed relative to the mAb to PE38 (IP30). Data are expressed as the mean +SD. HA, HA22; LR, HA22-LR; LR8M, HA22-LR-8M; ns, not significant; *, p<0.05

It is understood that the examples and embodiments described herein are for illustrative purposes only and that various modifications or changes in light thereof will be suggested to persons skilled in the art and are to be included within the spirit and purview of this application and scope of the appended claims. All accession numbers, publications, patents, and patent applications cited herein are hereby incorporated by reference in their entirety for all purposes.

What is claimed is:

1. An isolated Pseudomonas exotoxin A ("PE"), wherein said PE has residues 1-273 and 285-394 removed and substitutions of alanine, glycine or serine in place of amino acid residues D406, R432, R467, R490, R513, E548, K590 and Q592 corresponding to an amino acid residue of SEQ ID NO:1.

2. A PE of claim 1, wherein said PE further has a substitution of alanine, glycine or serine of at least one amino acid residue corresponding to an amino acid residue of SEQ ID NO:1 selected from the group consisting of D403, R412, R427, E431, R458, D461, R505, E522, R538, R551, R576 and L597.

3. A PE of claim 1, wherein said PE has an amino acid sequence of SEQ ID NO:2.

4. A PE of claim 1, wherein said PE has an amino acid sequence of SEQ ID NO:3.

5. A chimeric molecule comprising (a) a targeting moiety conjugated or fused to (b) a Pseudomonas exotoxin A ("PE"), wherein said PE has residues 1-273 and 285-394 removed and substitutions of alanine, glycine or serine in place of amino acid residues D406, R432, R467, R490, R513, E548, K590 and Q592 corresponding to an amino acid residue of SEQ ID NO:1.

6. A chimeric molecule of claim 5, wherein said PE further has a substitution of alanine, glycine or serine of at least one amino acid residue corresponding to an amino acid residue of SEQ ID NO:1 selected from the group consisting of D403, R412, R427, E431, R458, D461, R505, E522, R538, R551, R576 and L597.

7. A chimeric molecule of claim 5, wherein said PE has an amino acid sequence of SEQ ID NO:2.

8. A chimeric molecule of claim 5, wherein said PE has an amino acid sequence of SEQ ID NO:3.

9. A chimeric molecule of claim 5, wherein said targeting moiety is an antibody.

10. A chimeric molecule of claim 9, wherein said antibody is selected from the group consisting of an scFv, a dsFv, a Fab, a single domain antibody and a $F(ab')_2$.

11. A chimeric molecule of claim 9, wherein said antibody is against a cell surface antigen selected from the group consisting of CD19, CD21, CD22, CD25, CD30, CD33, CD79b, transferrin receptor, EGF receptor, mesothelin, cadherin and Lewis Y.

12. A chimeric molecule of claim 9, wherein said antibody is selected from the group consisting of B3, RFB4, SS1, MN, HN1, HN2 and HB21.

13. A chimeric molecule of claim 9, wherein said antibody has a variable light (VL) chain comprising three complementarity determining regions (CDRs), and a variable heavy (VH) chain comprising three CDRs, wherein (i) said VL CDR1 has the sequence QDIXXY (SEQ ID NOS:4-8), wherein XX is selected from SN, HG, GR, RG and AR;

(ii) said VL CDR2 has the sequence YTS;

(iii) said VL CDR3 has the sequence QQGNTLPWT (SEQ ID NO:9);

(iv) said VH CDR1 has the sequence GFAFSIYD (SEQ ID NO:10);

(v) said VH CDR2 has the sequence ISSGGGTT (SEQ ID NO:11);

(vi) said VH CDR3 has the sequence ARHSGYGXXXGVLFAY (SEQ ID NOS:12-16), wherein XXX is selected from SSY, THW, YNW, TTW and STY.

14. A chimeric molecule of claim 9, wherein said antibody has a variable light (VL) chain comprising three complementarity determining regions (CDRs), and a variable heavy (VH) chain comprising three CDRs, wherein (i) said VL CDR1 has the sequence QDIHGY (SEQ ID NO:5);

(ii) said VL CDR2 has the sequence YTS;

(iii) said VL CDR3 has the sequence QQGNTLPWT (SEQ ID NO:9);

(iv) said VH CDR1 has the sequence GFAFSIYD (SEQ ID NO:10);

(v) said VH CDR2 has the sequence ISSGGGTT (SEQ ID NO:11);

(vi) said VH CDR3 has the sequence ARHSGYGTHWGVLFAY.

15. A chimeric molecule of claim 5, wherein said targeting moiety is a cytokine, a lymphokine or a growth factor.

16. A composition comprising (a) a chimeric molecule comprising a targeting moiety conjugated or fused to a Pseudomonas exotoxin A ("PE"), wherein said PE has residues 1-273 and 285-394 removed and substitutions of alanine, glycine or serine in place of amino acid residues D406, R432, R467, R490, R513, E548, K590 and Q592 corresponding to an amino acid residue of SEQ ID NO:1, and (b) a pharmaceutically acceptable carrier.

17. A composition of claim 16, wherein said PE further has a substitution of alanine, glycine or serine of at least one amino acid residue corresponding to an amino acid residue of SEQ ID NO:1 selected from the group consisting of D403, R412, R427, E431, R458, D461, R505, E522, R538, R551, R576 and L597.

18. A composition of claim 16, wherein said PE has an amino acid sequence of SEQ ID NO:2.

19. A composition of claim 16, wherein said PE has an amino acid sequence of SEQ ID NO:3.

20. A composition of claim 16, wherein said targeting moiety is an antibody.

21. A composition of claim 20, wherein said antibody is selected from the group consisting of an scFv, a dsFv, a Fab, a single domain antibody and a $F(ab')_2$.

22. A composition of claim 20, wherein said antibody is against a cell surface antigen selected from the group consisting of CD19, CD21, CD22, CD25, CD30, CD33, CD79b, transferrin receptor, EGF receptor, mesothelin, cadherin and Lewis Y.

23. A composition of claim 20, wherein said antibody is selected from the group consisting of B3, RFB4, SS1, HN1, HN2, MN and HB21.

24. A composition of claim 20, wherein said antibody has a variable light (VL) chain comprising three complementarity determining regions (CDRs), and a variable heavy (VH) chain comprising three CDRs, wherein (i) said VL CDR1 has the sequence QDIXXY (SEQ ID NOS:4-8), wherein XX is selected from SN, HG, GR, RG and AR;

(ii) said VL CDR2 has the sequence YTS;

(iii) said VL CDR3 has the sequence QQGNTLPWT (SEQ ID NO:9);

(iv) said VH CDR1 has the sequence GFAFSIYD (SEQ ID NO:10);

(v) said VH CDR2 has the sequence ISSGGGTT (SEQ ID NO:11);

(vi) said VH CDR3 has the sequence ARHSGYGXXXGV-LFAY (SEQ ID NOS:12-16), wherein XXX is selected from SSY, THW, YNW, TTW and STY.

25. A composition of claim 20, wherein said antibody has a variable light (VL) chain comprising three complementarity determining regions (CDRs), and a variable heavy (VH) chain comprising three CDRs, wherein (i) said VL CDR1 has the sequence QDIHGY (SEQ ID NO:5);

(ii) said VL CDR2 has the sequence YTS;

(iii) said VL CDR3 has the sequence QQGNTLPWT (SEQ ID NO:9);

(iv) said VH CDR1 has the sequence GFAFSIYD (SEQ ID NO:10);

(v) said VH CDR2 has the sequence ISSGGGTT (SEQ ID NO:11);

(vi) said VH CDR3 has the sequence ARHSGYGTH-WGVLFAY (SEQ ID NO:13).

26. A composition of claim 16, wherein said targeting moiety is a cytokine, a lymphokine or a growth factor.

27. A method of inhibiting the growth of a cell bearing a target molecule, said method comprising contacting said cell with a chimeric molecule comprising (a) a targeting moiety that specifically binds said target molecule, and (b) a Pseudomonas exotoxin A ("PE"), wherein said PE has residues 1-273 and 285-394 removed and substitutions of alanine, glycine or serine in place of amino acid residues D406, R432, R467, R490, R513, E548, K590 and Q592 corresponding to an amino acid residue of SEQ ID NO:1, wherein contacting said cell with said chimeric molecule inhibits the growth of said cell.

28. A method of claim 27, wherein said PE further has a substitution of alanine, glycine or serine of at least one amino acid residue corresponding to an amino acid residue of SEQ ID NO:1 selected from the group consisting of D403, R412, R427, E431, R458, D461, R505, E522, R538, R551, R576 and L597.

29. A method of claim 27, wherein said PE has an amino acid sequence of SEQ ID NO:2.

30. A method of claim 27, wherein said PE has an amino acid sequence of SEQ ID NO:3.

31. A method of claim 27, wherein said targeting moiety is an antibody.

32. A method of claim 31, wherein said antibody is selected from the group consisting of an scFv, a dsFv, a Fab, a single domain antibody and a $F(ab')_2$.

33. A method of claim 31, wherein said antibody is against a cell surface antigen selected from the group consisting of CD19, CD21, CD22, CD25, CD30, CD33, CD79b, transferrin receptor, EGF receptor, mesothelin, cadherin and Lewis Y.

34. A method of claim 31, wherein said antibody is selected from the group consisting of B3, RFB4, SS1, HN1, HN2, MN and HB21.

35. A method of claim 31, wherein said antibody has a variable light (VL) chain comprising three complementarity determining regions (CDRs), and a variable heavy (VH) chain comprising three CDRs, wherein (i) said VL CDR1 has the sequence QDIXXY (SEQ ID NOS:4-8), wherein XX is selected from SN, HG, GR, RG and AR;

(ii) said VL CDR2 has the sequence YTS;

(iii) said VL CDR3 has the sequence QQGNTLPWT (SEQ ID NO:9);

(iv) said VH CDR1 has the sequence GFAFSIYD (SEQ ID NO:10);

(v) said VH CDR2 has the sequence ISSGGGTT (SEQ ID NO:11);

(vi) said VH CDR3 has the sequence ARHSGYGXXXGV-LFAY (SEQ ID NOS:12-16), wherein XXX is selected from SSY, THW, YNW, TTW and STY.

36. A method of claim 31, wherein said antibody has a variable light (VL) chain comprising three complementarity determining regions (CDRs), and a variable heavy (VH) chain comprising three CDRs, wherein (i) said VL CDR1 has the sequence QDIHGY (SEQ ID NO:5);

(ii) said VL CDR2 has the sequence YTS;

(iii) said VL CDR3 has the sequence QQGNTLPWT (SEQ ID NO:9);

(iv) said VH CDR1 has the sequence GFAFSIYD (SEQ ID NO:10);

(v) said VH CDR2 has the sequence ISSGGGTT (SEQ ID NO:11);

(vi) said VH CDR3 has the sequence ARHSGYGTH-WGVLFAY (SEQ ID NO:13).

37. A method of claim 27, wherein said targeting moiety is a cytokine, a lymphokine or a growth factor.

* * * * *